United States Patent [19]

Haughland et al.

[11] Patent Number: 5,443,986
[45] Date of Patent: Aug. 22, 1995

[54] ENZYMATIC ANALYSIS USING SUBSTRATES THAT YIELD FLUORESCENT PRECIPITATES

[75] Inventors: Richard P. Haughland; Zhijian Huang; Karen D. Larison; Yu-zhong Zhang, all of Eugene, Oreg.

[73] Assignee: Molecular Probes, Inc., Eugene, Oreg.

[21] Appl. No.: 88,894

[22] Filed: Jul. 6, 1993

Related U.S. Application Data

[62] Division of Ser. No. 748,860, Aug. 23, 1991, Pat. No. 5,316,906.

[51] Int. Cl.[6] ............ C12Q 1/00; C08G 63/48; A61K 37/02; C04B 35/00
[52] U.S. Cl. .................... 435/4; 435/28; 435/23; 435/25; 525/54.1; 546/109; 252/62.51; 530/300
[58] Field of Search ............ 435/4, 28, 23, 18, 25; 525/54.1; 546/33, 109, 153; 252/62.51; 530/300; 544/289, 249

[56] References Cited

U.S. PATENT DOCUMENTS

| 3,169,129 | 2/1965 | Rodgers et al. | 260/251 |
| 3,526,627 | 9/1970 | Brooks et al. | 260/251 |
| 3,655,664 | 4/1972 | Pater | 260/251 |
| 5,017,475 | 5/1991 | Harte et al. | 435/28 |

OTHER PUBLICATIONS

Leary, et al., Proc. Natl. Acad. Sci. 80, 4045 (1983).
Wolf, et al., Lab Invest. 15, 1132 (1966).
Menten, et al., Proc. Soc. Exp. Biol. Med. 51, 82 (1944).
Burstone, Enzyme Chemistry and Its Applications in the Study of Neoplasm, p. 160 (Academic Press 1962).
(List continued on next page.)

Primary Examiner—David A. Redding
Assistant Examiner—Louise N. Leary
Attorney, Agent, or Firm—Allegra J. Helfenstein; Anton E. Skaugset

[57] ABSTRACT

Activity of enzymes and enzyme conjugates is detected using novel substrates made from a class of fluorophores, generally including quinazolinones (quinazolones), benzimidazoles, benzothiazoles, benzoxazoles, quinolines, indolines, and phenanthridines, having the general formula:

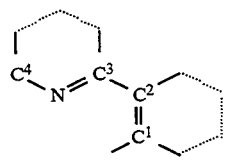

where carbon atoms of $-C^1=C^2-$ are joined to complete a first 5- or 6-membered aromatic ring which optionally contains one of the hetero atoms N, O or S, and carbon atoms of $-C^4-N=C^3-$ are joined to complete a second 5- or 6-membered aromatic ring that contains a nitrogen between $C^3$ and $C^4$ and optionally contains an additional hetero atom N, O or S, where the first and second aromatic rings may be joined by a 5- or 6-membered bridging ring that contains at least the $C^2$ from the first aromatic ring and the $C^3$ from the second aromatic ring, where each of the first and second aromatic rings may be fused to at least one additional aromatic ring that may contain at least one of the hetero atoms N, O or S, and where each of said aromatic rings may be further modified by substitution of any hydrogens on an aromatic carbon by substituents that are halogen, nitro, cyano, aryl, lower alkyl (1–4 carbons), perfluoroalkyl (1–4 carbons), or alkoxy (1–4 carbons), or any combination thereof; and the fluorophore is covalently linked to a blocking group through an oxygen $-O-$ at $C_1$; such that removal of the blocking group by enzyme activity yields a precipitate.

39 Claims, 4 Drawing Sheets

Step 1

OTHER PUBLICATIONS

Ziomek, et al., Histochem. Cytochem. 38 (3), 437 (1990).
Springer, et al., Histochem. and Cytochem. 39, 231 (1991).
Hopman, et al., Molecular Neuroanatomy, pp. 43, Elsevier Science Publishers (1988).
Hein, et al., J. Am. Chem. Soc. 79, 427 (1957).
Naumann & Langhals, Synthesis 279 (Apr. 1990).
Catalan, et al., J. Am. Chem. Soc. 112, 747 (1990).
Sinha & Dogra, Chem. Physics 102, 337 (1986).
Orlando, et al., Chem. Comm. 23, 1551 (1971).
Williams & Heller, J. Phys. Chem. 74, 4473 (1970).
Stephens, et al., J. Chem. Soc. 2971 (1949).
Delegiorgiev, Dyes and Pigments 12, 243 (1990).
Kresze, et al., Z. Naturforschung 10B, 370 (1955).
Farley, et al., J. Biol. Chem. 225, 4680 (1980).
Winkelman, et al., Am. J. Clin. Pathol. 57, 625, (1972).
Carlsson, et al., Biochem. J. 173, 723 (1976).
*Flow Cytometry and Sorting,* Melamed, Lindmo, and Mendelsohn, Wiley-Liss (1990).
Stryer, L., *Biochemistry,* pp. 189, W. H. Freeman and Company, New York, 1988.
Capaldi and Hayashi, FEBS Lett 26, 4229–4238 (1972).
Zhang, Lindorfer, and Capaldi. Biochemistry, 27, 1389–1394 (1988).
Harlow and Lane, Antibodies, A Laboratory Manual, Cold Springs Harbor Lab (1988).

Step 1

Step 2

ENZYMATIC ANALYSIS USING SUBSTRATES THAT YIELD FLUORESCENT PRECIPITATES

This invention was made with U.S. Government support under grant GM 38987 awarded by the U.S. National Institutes of Health. The U.S. Government has certain rights in this invention.

This is division of application number 07/748,800, filed Aug. 23, 1991, now U.S. Pat. No. 5,316,906.

FIELD OF THE INVENTION

This invention relates to a class of novel fluorogenic substrates for detecting enzyme activity, particularly that of glycosidase, phosphatase, and sulfatase enzymes. The enzyme acts on the appropriate substrate to yield fluorescent products that are specifically formed, nontoxic, and insoluble in aqueous systems.

BACKGROUND OF INVENTION

Detection of enzyme activity is useful in the analysis of a biological or chemical sample, such as whole organisms, cells or cell extracts, biological fluids, or chemical mixtures. For example, information about metabolism, disease state, the identity of microorganisms, the success of a genetic manipulation, or the quantity of toxins, can be gained from evaluating the activity of certain enzymes. Furthermore enzyme conjugates are often used as sensitive bioanalytical tools for detection of analytes.

Enzyme activity is often detected through the use of a synthetic substrate. The endogenous substrates of an enzyme are used in designing synthetic substrates. Several glycosidase enzymes are known to target specific glycosides (R—O—Gly) to yield the corresponding carbohydrate and an organic alcohol or phenol (R—OH). Phosphatase enzymes catalyze the conversion of certain phosphate monoesters (R—O—P(O)-(OH)$_2$) to inorganic phosphate (P$_i$) and an organic alcohol (R—OH). Similarly, organic alcohols or phenols result when sulfatase enzymes liberate inorganic sulfate from some sulfate monoesters (R—O—SO$_3$H) or when guanidinobenzoatase enzymes hydrolyze aryl esters of p-guanidinobenzoic acid (R—O—(C=O)—C$_6$H$_4$—N-H—(C=NH)—NH$_2$). Carboxylic acid esters (R—O—(C=O)—R') are hydrolyzed by esterase enzymes to alcohols and acids. Cytochrome enzymes oxidize aryl alkyl ethers to give the phenol and an aldehyde or acid.

Most phosphatase and sulfatase enzymes are nonselective for the structure of the alcohol. Two types of phosphatase enzymes have been identified, however, that have different optimal pH for their enzymatic activity (pH optima about 10 and about 5 respectively). The aryl sulfatase enzyme most closely resembles the acid phosphatase in pH optimum and substrate turnover. Guanidinobenzoatase is a cell surface protease characteristic of several human tumor cell lines, which is not detectable in normal human cell strains. Esterases have structural requirements that range from those that hydrolyze esters of the lower carboxylic acids (usually < about 4 carbons) to the "lipase" enzymes that optimally hydrolyze esters of the longer carboxylic acids (usually > about 8 carbons). There are several cytochrome enzymes (isoenzymes) that differ in their ability to metabolize aryl ethers depending on the source of the enzyme. Table 1 lists some commonly investigated enzymes and their target groups.

TABLE 1

REPRESENTATIVE ENZYMES

| E.C. NO. | ENZYME | TARGET GROUP |
|---|---|---|
| 3.2.1.20 | α-Glucosidase | α-D-Glucose |
| 3.2.1.21 | β-Glucosidase | β-D-Glucose |
| 3.2.1.22 | α-Galactosidase | α-D-Galactose |
| 3.2.1.23 | β-Galactosidase | β-D-Galactose |
| 3.2.1.24 | α-Mannosidase | α-D-Mannose |
| 3.2.1.25 | β-Mannosidase | β-D-Mannose |
| 3.2.1.30 | N-Acetyl-β-glucosaminidase | β-D-N-Acetyl-Glucosamine |
| 3.2.1.31 | β-Glucuronidase | β-D-Glucuronic Acid |
| 3.2.1.38 | β-D-Fucosidase | β-D-Fucose |
| 3.2.1.51 | α-L-Fucosidase | α-L-Fucose |
| 3.2.1.— | β-L-Fucosidase | β-L-Fucose |
| 3.2.1.76 | L-Iduronidase | α-L-Iduronic Acid |
| 3.2.1.4 | Cellulase | β-D-Cellobiose |
| 3.2.1.— | α-Arabinopyranosidase | α-L-Arabinopyranose |
| 3.2.1.37 | β-Xylosidase | β-D-Xylose |
| 3.2.1.18 | α-N-Acetyl-neuraminidase | α-D-N-Acetyl-neuraminic acid (Sialic acid) |
| 3.1.1— | guanidinobenzoatase | aryl esters of p-guanidinobenzoic acid |
| 3.1.3.1 | alkaline phosphatase | aryl or alkyl phosphate monoesters |
| 3.1.3.2 | acid phosphatase | aryl or alkyl phosphate monoesters |
| 3.1.6.1 | aryl sulfatase | aryl sulfate monoesters |
| 3.3.3.41 | 4-nitrophenyl phosphatase | aryl phosphates |

The synthetic substrates for many enzymes, including those in Table 1 as well as many esterases and cytochrome enzymes, are consistently based on the same organic alcohol or phenolic precursors, differing only by the nature of the leaving group (e.g. phosphate, sulfate, guanidinobenzoate, carboxylic acid, carbohydrate, or alkyl alcohol). The synthetic substrate should not inhibit the enzymatic reaction so that the enzyme can produce enough product so that it can be detected (enzyme amplification of the detection product). Most synthetic substrates have been designed so that the presence of the enzyme (or enzyme conjugate) results in a detectable phenolic product, e.g. formation of a soluble colored or fluorescent product or formation of a precipitate.

Common substrates that yield soluble chromogenic (but nonfluorescent) products include phosphate or sulfate monoesters or glycosides of o-nitrophenol, p-nitrophenol, thymolphthalein and phenolphthalein. Fluorogenic substrates derived from such phenols as various 7-hydroxycoumarins, 3-O-methylfluorescein, 8-hydroxypyrene-1,3,6-trisulfonic acid, flavones or various derivatives of α-or β-naphthols typically yield soluble fluorescent products. Although assays based on fluorescent products are generally preferred because of their greater sensitivity, they are deficient in a number of properties for analytical measurement of enzyme activity in vivo and in vitro.

None of the reported fluorogenic substrates that yield soluble products are optimally detected below a pH of about 6. With many substrates it is necessary to adjust the pH of the dye product to above 10 to obtain the maximum fluorescence efficiency. Assays that require such a change in pH or the addition of other development reagents are not readily adapted for highly automated analytical procedures. In addition, soluble reaction products, whether fluorescent or colored, readily diffuse away from the site of activity, especially in in vivo applications.

Certain substrates for phosphatase, sulfatase and some glycosidase enzymes are known to yield colored precipitates that are not fluorescent. The best known of these are 5-bromo-4-chloro-3-indolyl phosphate (BCIP) [Leary, et al., PROC. NATL. ACAD. SCI. 80, 4045 (1983)], 5-bromo-4-chloro-3-indolyl galactoside (X-Gal), several other "X-glycosides" that are similar to X-gal and the corresponding 5-bromo-4-chloroindolyl sulfate [Wolf, et al., LAB. INVEST. 15, 1132 (1966)]. Following enzymatic hydrolysis, the colorless 3-hydroxyindole intermediates are converted to insoluble indigoid dyes by oxidation with a second reagent or more slowly by molecular oxygen.

Menton, et al., PROC. SOC. EXP. BIOL. MED. 51, 82 (1944), introduced a two step technique in which certain phenolic products, liberated by hydrolytic enzymes, are subsequently coupled to a diazonium salt. The technique yields chromophoric, but nonfluorescent, diazo dye products. Burstone, ENZYME CHEMISTRY AND ITS APPLICATIONS IN THE STUDY OF NEOPLASM, pg. 160 (Academic Press 1962) introduced simplified simultaneous and post-coupling azo dye techniques using naphthol-AS-phosphates and sulfates, as the enzyme substrates.

A modification of the two step technique Ziomek, et al., HISTOCHEM. CYTOCHEM. 38 (3), 437 (1990), reportedly yields a red fluorescent azo dye precipitate that is useful for histochemical demonstration of phosphatase activity. The coupling reaction of the diazo color-forming reagent must be accomplished at an alkaline pH. While this pH may be adequate for histochemical detection of alkaline phosphatase activity, it does not permit continuous detection of the activity of acid phosphatase and aryl sulfatase enzymes and is suboptimal for detection of $\beta$-galactosidase (pH optimum 7.2), since these enzymes all have extremely low activity in alkaline medium. Furthermore, the diazo coupling reaction is not specific for the phenols formed by the enzymatic reaction. Therefore the presence of intrinsic phenolic contaminants in the test solution or the biological fluid can yield false positive signals. All of the above methods suffer from weak and somewhat nonspecific fluorescent staining of enzyme activity.

Enzyme-amplification techniques are used in histochemistry and cytochemistry to localize specific antigens by microscopy. Success of this technique depends on an efficient site-specific deposit of enzymatic products that contrast well with the underlying cellular structures. Colored precipitate formed by hydrolysis of known chromophoric precipitating substrates such as X-gal can be well visualized at discrete loci in cells or tissues using light microscopy, if the sample has appreciable quantities of the target molecules. It has been reported that the chromophoric precipitating substrate for alkaline phosphatase, when coupled with a digoxigenin-labeled probe and anti-digoxigenin conjugated with alkaline phosphatase, can stain nerve growth factor mRNA at a higher sensitivity and resolution than a standard isotope label method [Springer et al., HISTOCHEM. AND CYTOCHEM. 39, 231 (1991)]. However, the enzymatic products from the chromophoric substrates are not sufficient to form a visible precipitate that contrasts well with cellular structures when a single molecule of the analyte must be detected, because the chromophoric signal is insufficient for detection. The fluorescent precipitate of this invention, in contrast, provides a more easily detectable signal in smaller amounts.

In recent years, numerous nonradioactive approaches have been developed and refined for in situ hybridization [Hopman et al., MOLECULAR NEUROANATOMY, pp 43, Elsevier Science Publishers (1988)]. All of these nonradioactive techniques are generally able to detect specific mRNA in situ without difficulty. In contrast, the nonradioactive methods for detecting a specific gene which exists in few or even single copies in a cell's genome using biotinylated probes, require oligonucleotides that contain several thousand bases in order to allow for sufficient incorporation of the biotin (or other) label. In practical terms, any probe shorter than about 2,000 bases will not result in visible signals sufficient to detect few or single copies in the cell genome utilizing either the colored precipitates or fluorescence microscopy. The need for a probe of such long length severely limits the ease and flexibility of the probe design because preparation involves such time-consuming techniques. Because of their stronger accumulated signal, the substrates of this invention can be used with shorter oligonucleotide probes.

The substrates of this invention also differ significantly from substrates previously described in that most known fluorogenic substrates yield products that are appreciably fluorescent only in the solution phase, whereas the preferred substrates from this invention are virtually nonfluorescent except in the solid phase. In addition they yield insoluble, highly fluorescent products without requiring addition of a color-developing and precipitating reagent. Furthermore, the subject substrates are specific for a particular enzymatic activity, and are optimally reactive at or below physiological pH. As a result of these characteristics, the substrates of this invention can detect the activity of a wide variety of enzymes and enzyme-related analytes, in living cells, in extracts of living cells, in biological fluids, in biopsy samples, in vivo and in vitro, without requiring any preprocessing of the samples by concentration, centrifugation, or filtration and without addition of secondary reagents.

Some of the fluorescent dyes used to prepare the subject substrates are already known, e.g. U.S. Pat. No. 3,169,129 2-Ortho-hydroxy-phenyl-4-(3H)-quinazolinones to Rodgers, et al. (1965) (quinazolinones); Hein, et al., *The Use of Polyphosphoric Acid in the Synthesis of 2-Aryl- and 2-Alkyl-substituted Benzimidazoles, Benzoxazoles and Benzothiazoles,* J. AM. CHEM. SOC. 79, 427 (1957) (benzimidazoles, benzoxazoles and benzothiazoles); and Naumann & Langhals, *A Simple Synthesis of Dihydroxybipyridyls,* SYNTHESIS 279 (Apr. 1990) (dihydroxybipyridyls). It has been recognized that several of the dyes have very low solubility, particularly in water, and that the compounds are fluorescent in the solid state. The large Stokes shift characteristic of some compounds in this class of dyes has also been described. There have been several studies of the fluorescence mechanism of this class of compounds which has been related to a high degree of photostability. Catalan, et al., *Photoinduced Intramolecular Proton Transfer as the Mechanism of Ultraviolet Stabilizers: A Reappraisal,* J. AM. CHEM. SOC. 112, 747 (1990); Sinha & Dogra, *Ground State and Excited State Prototropic Reactions in 2-(o-Hydroxyphenyl)benzimidazole,* CHEM. PHYSICS 102, 337 (1986); Orlando, et al., *Red- and Near-infrared-luminescent Benzazole Derivatives,* CHEM. COMM. 23, 1551 (1971); and Williams & Heller, *Intramolecular Proton Transfer Reactions in Excited Fluorescent Compounds,* J. PHYS. CHEM. 74, 4473 (1970). None of the references, however, indicate the use of these dyes as fluorogenic substrates.

Orlando, et al., supra at 1552, citing Williams & Heller supra noted that replacement of an o-hydroxyphenyl group by an o-methoxyphenyl group results in nonfluorescent benzazoles. An alkoxy group was the only blocking group described in the reference, however, and there was no indication that blocking groups could be selected to monitor the presence or activity of enzymes.

DESCRIPTION OF THE DRAWINGS

FIG. 1 is a diagram of the formation pathway of some typical glycosidase substrates. In step 1, the fluorophore is glycosylated using a modified Koenigs-Knorr methodology in which a protected carbohydrate group is added to the hydroxyphenyl-quinazolinone. After isolation of the protected intermediate by column chromatography or by precipitation of the remaining starting material combined with recrystalization or trituration, the protective groups are removed (step 2) to yield a nonfluorescent 2'-glycosidyloxyphenylquinazolinone.

Figure 1:
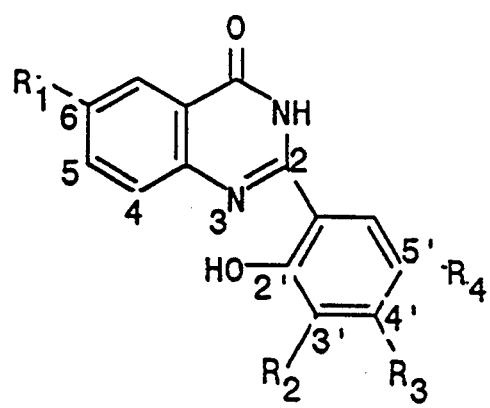
FIG. 1: Synthesis of Substrate.
Figure 1:
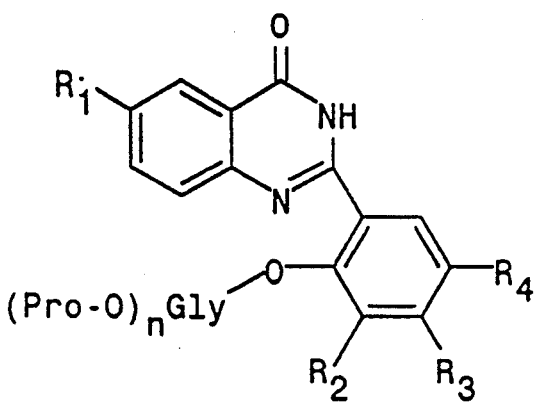
Figure 1:
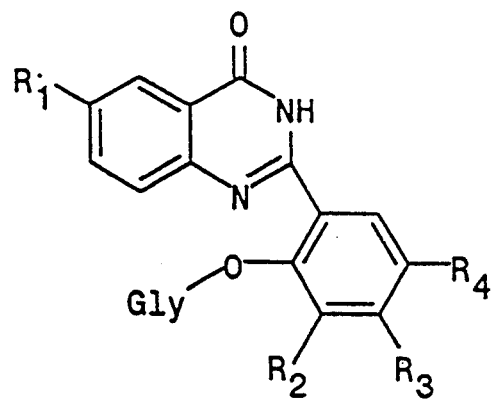

2A) Fluorescence characterization of a fluorogenic precipitating substrate: a. emission of 2 mM 2-(4'-methoxy-2'-phosphoryloxyphenyl)quinazolinone (3e); b. emission of the precipitate resulting from incubation of the substrate (2 mM) in the presence of excess alkaline phosphatase; c. emission following dissolution of the precipitate. The emission measurements were made in 0.1M TRIS pH 10.3 containing 50 mM NaCl, 10 mM $MgCl_2$ and 0.1 mM $ZnCl_2$ using a Perkin-Elmer LS-50 fluorometer with excitation at 400 nm, excitation slit 3.0 nm and emission slit 2.5 nm.

2B) Coexistence of fluorescence and precipitation: 5 mM 2-(4'-methoxy-2'-phosphoryloxyphenyl)-quinazolinone (3e), in 0.1M TRIS pH 10.3 containing 50 mM NaCl, 10 mM $MgCl_2$ and 0.1 mM $ZnCl_2$, yields 210 units of fluorescence by action of 10 μg/mL alkaline phosphatase in 20 seconds. The fluorescence can be eliminated by addition of 0.6% Triton X-100 as a result of precipitate dissolution.

2C) Light-scattering increase as a result of precipitation: 2 mM 2-(4'-methoxy-2'-phosphoryloxyphenyl)quinazolinone (3e) scattering increases from 450 units to beyond the detection limit of 1000 units in 20 seconds by action of 10 μg/mL alkaline phosphatase, showing rapid formation of a precipitate. The enzymatic reaction was in 0.1M TRIS pH 10.3 containing 50 mM NaCl, 10 mM $MgCl_2$ and 0.1 mM $ZnCl_2$. The scattering measurement was made in a Perkin-Elmer LS-50 fluorometer with 5 nm slits and a coincident excitation and emission wavelength of 420 nm.

2D) Critical concentration: Various concentrations of 2-(4'-methoxy-2'-phosphoryloxyphenyl)quinazolinone (3e) were reacted with 50 μL of excess alkaline phosphatase in 200 μL solution of 0.1M TRIS≧pH 10.3 containing 50 mM NaCl, 10 mM $MgCl_2$ and 0.1 mM $ZnCl_2$. The resulting precipitate and fluorescence were measured in a CytoFluor fluorescence plate reader (Millipore) with excitation at 360 nm, emission at 460 nm using sensitivity setting 3. The figure shows a critical concentration of 2.5 mM.

2E) pH dependence of precipitation: 2-(4'-Methoxy-2'-phosphoryloxyphenyl)quinazolinone(3e) was reacted with 50 μL of excess alkaline phosphatase in 150 μL solution of 0.1M TRIS pH 10.3 containing 50 mM NaCl, 10 mM $MgCl_2$ and 0.1 mM $ZnCl_2$, 0.6 mM. The mixture was titrated using 50 μL of various concentrations of HCl to obtain the desired pH, then measured in a CytoFluor fluorescence plate reader with excitation at 360 nm and emission at 460 nm using sensitivity setting 3. The figure shows a $pK_a$ of about 8.8.

SUMMARY OF THE INVENTION AND DESCRIPTION OF PREFERRED EMBODIMENTS

This invention describes novel substrates used to measure enzyme activity. The substrates are nonfluorescent but react with enzymes to yield fluorescent phenolic products that are specifically formed, nontoxic to the cells, and precipitate without inactivating the enzyme. The phenolic product may result from hydrolysis of a phenolic ester or a phenolic glycoside, e.g. by phosphatase, sulfatase, glycosidase and esterase enzymes. Alternatively, the phenolic product may be formed by oxidation of aryl alkyl ethers, e.g. by cytochrome enzymes.

The preferred substrates of this invention are blocked fluorophores represented by the formula:

BLOCK-O-$X_{fl}$ where the fluorophore $X_{fl}$ contains a minimum of 2 aromatic rings, two of which are typically linked rather than fused together. The aromatic rings include unsaturated heterocyclic ring structures. Each of the two linked aromatic rings may be fused to additional aromatic rings. Typically, at least one of the aromatic rings is fused to at least one additional aromatic ring. In general, fusion of one of the linked aromatic rings to at least one additional aromatic ring increases the wavelength at which the solid product can be excited and at which the fluorescence can be detected, which is beneficial for some applications. Fusion to an additional ring also typically results in the product becoming less soluble in water, which is favorable to precipitation.

BLOCK is a group that changes the excitation or emission properties (i.e. absorbance or fluorescence) of the fluorophore and is capable of being cleaved from the remainder of the substrate molecule by action of an enzyme. Preferably BLOCK blocks the long wavelength (greater than about 450 nm) fluorescence of the fluorophore. BLOCK is selected to be specific for the enzyme of interest. Typically, BLOCK is a monovalent moiety derived by removal of a hydroxy group from phosphate, from sulfate or a biologically compatible salt thereof; or a monovalent moiety derived by removal of a hydroxy group from an alcohol or from a carboxy group of an aliphatic, aromatic or amino acid or of a peptide; or a monovalent moiety derived by removal of the anomeric hydroxy group from a mono- or polysaccharide. Preferred monovalent blocking groups include the target groups listed in Table 1, which includes some of the enzymes that will cleave such groups from the substrate.

When BLOCK is separated from the remainder of the substrate molecule by action of an enzyme, the result is a visible precipitate. A visible precipitate means it is detectable by a light sensitive mechanism, e.g. a change in spectral (excitation/emission) properties, a change in light scattering, or visible crystal formation. Preferably the precipitate is fluorescent. The favorable pH range for precipitation and detection of the fluorescent products is from below about pH 2 to above about pH 11, most favorably in the range of pH 5-8, which encompasses the physiological pH for in vivo applications.

The visible precipitate generally has the formula H—O—$X_{fl}$, where $X_{fl}$ is a fluorophore of the formula:

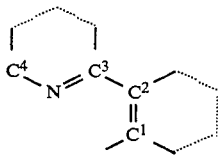

that is covalently linked through $C^1$ to the oxygen —O—.

The carbon atoms of —$C^1$=$C^2$— are joined so as to complete a first 5- or 6-membered aromatic ring that may contain at least one of the hetero atoms N, O or S. Commonly the —$C^2$=$C^1$—O—H portion of the fluorescent precipitate defines a phenol or a naphthol. Less commonly this portion of the fluorescent precipitate contains a hetero atom.

The carbon atoms of —$C^4$—N=$C^3$— are likewise joined so as to complete a second 5- or 6-membered aromatic ring that contains at least the one nitrogen heteroatom that is between $C_3$ and $C_4$. This second ring may also contain at least one additional hetero atom N, O or S, as well as oxo, thiooxo, sulfone, or amino functionalities.

The first and second 5- or 6-membered aromatic rings may be joined by a bridging ring between said first and second rings. The bridging ring includes at least $C^2$ and $C^3$ and can contain a heteroatom N, O or S. The bridging ring may be a 5- or 6-membered ring and may be saturated or unsaturated.

Each of the first and second 5- or 6-membered aromatic rings may be fused to at least one additional aromatic ring that may contain at least one of the hetero atoms N, O or S. Preferably, the fluorophore contains at least three aromatic rings, two of which are fused. Typically the second aromatic ring which contains at least one nitrogen heteroatom is fused to a third aromatic ring.

Each of the aromatic rings may be further modified by substitution of any hydrogen(s) on an aromatic carbon with a halogen atom, lower alkyl (about 1-4 carbons), perfluoroalkyl (about 1-4 carbons), alkoxy (about 1-4 carbons), nitro, cyano or aryl, or any combination thereof. The preferred halogen substituents are F, Cl or Br. Halogen and alkoxy substituents on the aromatic rings appear to have a beneficial effect both on reducing the solubility and improving the fluorescence properties of the fluorescent solid.

In one embodiment of the invention, H—O—$X_{fl}$ has the structure:

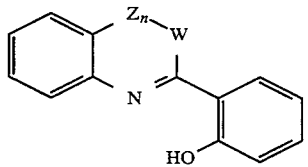

where W is ($CH_3)_2$C(isopropylidene), —$CH_2$—, —CH=(methine), S, O, or —(N—R)— wherein R is H or lower alkyl (1-4 carbons); and Z is —(C=O)— or —CH=; and n is 1 or 0. When W is —(N—R)— and Z is —(C=O)—, the products are quinazolinones (also referred to as quinazolones). When W is —(N—R)— and Z is absent (n=0), the product are benzimidazoles. When W is S and Z is absent (n=0), the products are benzothiazoles. When W is O and Z is absent (n=0), the products are benzoxazoles. When W and Z are each methine, the products are quinolines. When W is isopropylidene and Z is absent (n=0), the products are indolines.

When the first aromatic ring and the second aromatic ring are both 6-membered rings that together form a 5- or 6- membered bridging ring between them, the products are phenanthridines. The bridging ring may be saturated or unsaturated. When $X_{fl}$ is a phenanthridine, the precipitate H—O—$X_{fl}$ has the structure:

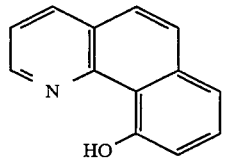

In another embodiment of the invention, the fluorophore $X_{fl}$ is a quinazolinone, benzimidazole, benzothiazole, benzoxazole, quinoline, an indoline, or a phenanthridine; and at least one of the aromatic rings is further modified by substitution of one or more hydrogen atoms on an aromatic carbon. One or more substituent(s), which may be the same or different, are F, Cl, Br, lower alkyl, perfluoroalkyl, alkoxy, nitro, cyano or aryl, or any combinations thereof.

In yet another embodiment of the invention, the fluorophore $X_{fl}$ is similar to a quinazolinone, benzimidazole, benzothiazole, benzoxazole, quinoline or an indoline but is further modified in that at least one of the aromatic rings is fused to at least one additional aromatic ring that may contain at least one of the hetero atoms N, O or S.

The preferred fluorogenic substrates for this invention have one or more of the following properties:

1) generally soluble but nonfluorescent in water but releasing a highly fluorescent solid product in an aqueous solution containing the substrate and the specific enzyme;

2) a low residual solubility and rapid precipitation rate for the solid product released by action of the enzyme;

3) reactive over a wide range of pH, generally below a pH of about 11;

4) can be prepared with a variety of blocking groups for the detection of the corresponding enzymes;

5) a p$K_a$ for the phenolic moiety of greater than about 8.0;

6) an excitation maximum of the solid product of greater than about 340 nm;

7) Stokes shift of the emission from the solid product of greater than about 100 nm;

8) high resistance of the fluorescent solid product to bleaching by incident light.

Preparation of Fluorophores ($X_{fl}$):

The preferred fluorescent dyes used in preparation of the fluorogenic substrates generally fall into the subclasses quinazolinones (Tables 2 and 3), quinolines, benzoxazoles, benzimidazoles, benzothiazoles (Table 4), indolines and phenanthridines. Schiffs bases (Table 5), which are similar in structure and also form fluorescent precipitates, are less preferred because they are relatively unstable in vivo.

Preparation of a number of the preferred fluorophores is described herein as a means of illustrating the breadth of the reaction. The descriptions are meant to illustrate, and not to limit the choice of reactants and reaction conditions that can be used to prepare the requisite fluorogenic substrates. By appropriate choice of substituents, in particular, the properties of solubility, fluorescence intensity and wavelengths and product photostability can be modified.

Table 2 lists representative 4(3H)-quinazolinones, their spectra and the visible color of the fluorescent crystals, according to the formula:

1) By heating of equimolar amounts of an anthranilamide with an aromatic aldehyde in the presence of catalytic amounts of p-toluenesulfonic acid (TsOH), a dihydroquinazolinone is formed, which is oxidized by a suitable oxidizing agent such as dichlorodicyanoquinone (DDQ) to the corresponding quinazolinone (Example 1).
2) By reaction of isatoic anhydrides with salicylamides in the presence of catalytic amounts of base in an inert solvent (U.S. Pat. No. 3,655,664 to Pater (1972) and Example 2).
3) U.S. Pat. No. 3,526,627 to Brooks (1970).

Table 3 lists representative benzo-4(3H)-quinazolinones their spectra and the visible color of the fluorescent crystals. The compounds in Table 3 are prepared by similar procedures as used for the compounds in

TABLE 2

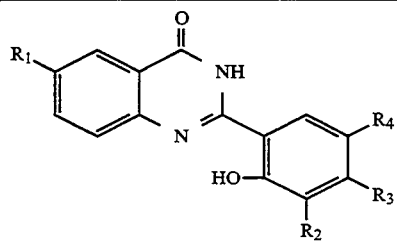

4-(3H)-quinazolinones (a)

| # | 4-(3H)-quinazolinones | $R_1$ | $R_2$ | $R_3$ | $R_4$ | mp [°C.] | Yield [%] | $EM_{max}{}^2$ | Color[1] |
|---|---|---|---|---|---|---|---|---|---|
| 1a | 2-(2'-hydroxyphenyl) | H | H | H | H | 297–298 | 64 | 490 | b-g |
| 2a | 2-(2'-hydroxy-5'-methoxyphenyl)- | H | H | H | OCH$_3$ | 290–292 | 89 | 550 | y |
| 3a | 2-(2'-hydroxy-5'-nitrophenyl)- | H | H | H | NO$_2$ | >350 | 74 | 470 | b |
| 4a | 2-(2'-hydroxy-4'-methoxyphenyl)- | H | H | OCH$_3$ | H | 284–286 | 35 | 450 | b |
| 5a | 2-(2'-hydroxy-4'-methoxyphenyl)-6-nitro- | NO$_2$ | H | OCH$_3$ | H | >350 | 42 | | b |
| 6a | 2-(2'-hydroxy-5'-methoxyphenyl)-6-chloro- | Cl | H | H | OCH$_3$ | 342–344 | 70 | 550 | y |
| 7a | 2-(5'-chloro-2'-hydroxyphenyl)-6-chloro- | Cl | H | H | Cl | >350 | 70 | 510 | y-g |
| 8a | 2-(2'-hydroxyphenyl)-6-chloro- | Cl | H | H | H | 336–338 | 30 | 500 | y-g |
| 9a | 2-(5'-chloro-2'-hydroxyphenyl)- | H | H | H | Cl | >350 | 60 | 510 | y-g |
| 10a | 2-(2'-hydroxy-4'-methoxyphenyl)-6-chloro- | Cl | H | OCH$_3$ | H | >350 | 64 | | b-g |
| 11a | 2-(3',5'-dichloro-2'-hydroxyphenyl)-6-chloro- | Cl | Cl | H | Cl | >350 | 45 | 550 | y |
| 12a | 2'-(3',5'-dichloro-2'hydroxyphenyl)- | H | Cl | H | Cl | >350 | 75 | | y-g |
| 13a | 2-(2'-hydroxy-5'-nitrophenyl)-6-nitro- | NO$_2$ | H | H | NO$_2$ | >350 | 96 | 525 | y-g |
| 14a | 2-(2'-hydroxy-5'-nitrophenyl)-6-chloro- | Cl | H | H | NO$_2$ | >350 | 86 | 480 | g |
| 15a | 2-(2'-hydroxyphenyl)-6-nitro- | NO$_2$ | H | H | H | >350 | 63 | 560 | y |
| 16a | 2-(5'-chloro-2'-hydroxyphenyl)-6-nitro- | NO$_2$ | H | H | Cl | >350 | 69 | | y |
| 17a | 2-(2-hydroxynaphthyl)- | | | | | 352-354 | 94 | | nf |
| 18a | bis-2,5-[4-(3H)-quinazolinoyl]-hydroquinone- | | | | | >350 | 8 | | r |

[1]Color of fluorescence: b-g = blue-green, y = yellow, b = blue, y-g = yellow-green, g = green, nf = non-fluorescent, r = red.
[2]Emission max. of solid [nm].

Among the methods that have been successfully utilized to prepare the subject quinazolinones dyes are the following:

Table 2 but starting with appropriately substituted aminonaphthalenecarboxylic acid derivatives.

TABLE 3 benzo-4-(3H)-quinazolinones according to the formula:

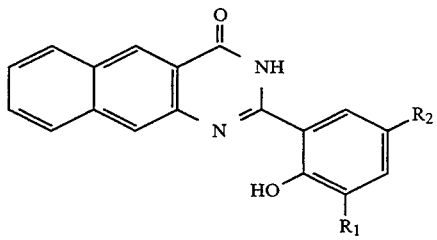

| # | benzo-4-(3H)-quinazolinones | R₁ | R₂ | mp [°C.] | Yield [%] | EM$_{max}$ of solid [nm] | Color[1] |
|---|---|---|---|---|---|---|---|
| 1b | 2-(2'-hydroxyphenyl) | H | H | >350 | 49 | ~510 | y-g |
| 2b | 2-(2'-hydroxy-5'-methoxyphenyl)- | H | OCH₃ | 356–58 | 28 | ~570 | |
| 3b | 2-(5'-chloro-2'-hydroxyphenyl)- | H | Cl | >350 | 57 | ~510 | y-g |
| 4b | 2-(3',5'-dichloro-2'-hydroxyphenyl)- | Cl | Cl | >350 | 75 | ~550 | y |

[1]Color of fluorescence: y-g = yellow-green, y = yellow.

Table 4 lists representative benzoxazoles, benzimidazoles and benzothiazoles, their spectra and the visible color of the fluorescent crystals according to the formula:

TABLE 4

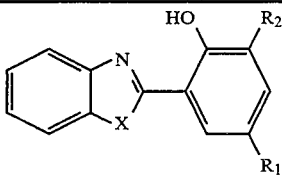

benzoxazoles, benzimidazoles and benzothiazoles

| # | Compound | R₁ | R₂ | X | mp [°C.] | Emission wavelength λ$_{max}$ [nm], | Color[1] |
|---|---|---|---|---|---|---|---|
| 1c | 2-(2'-hydroxyphenyl)benzoxazole | H | H | O | 126 | | b |
| 2c | 2-(2'-hydroxyphenyl)benzimidazole | H | H | NH | 242 | | b |
| 3c | 2-(2'-hydroxyphenyl)benzothiazole | H | H | S | 127–28 | 520 | y-g |
| 4c | 2-(2'-hydroxynaphthyl)benzothiazole | H | H | S | 110–12 | 520 | y-g |
| 5c | 2-(5'-amino-2'-hydroxyphenyl)benzothiazole | NH₂ | H | S | — | 660 | r |
| 6c | 2-(2'-hydroxy-5'-nitrophenyl)benzothiazole | NO₂ | H | S | 210–12 | 520 | y-g |
| 7c | 2-(3',5'-dichloro-2'-hydroxyphenyl)benzothiazole | Cl | Cl | S | 186–88 | 550 | y |
| 8c | 2-(2'-hydroxy-5'-methoxy)benzothiazole | OCH₃ | H | S | 74–76 | 600 | o |
| 9c | 2-(2',5'-dihydroxyphenyl)benzothiazole | OH | H | S | 192–94 | 550 | y |

[1]Color of fluorescence: b = blue, y-g = yellow-green, r = red, y = yellow, o = orange.

Fluorophores of this type are conveniently prepared from appropriately substituted derivatives of o-aminophenol, o-aminothiophenol and o-phenylenediamine and the corresponding substituted derivatives of a benzoic, naphthoic or polycyclic aromatic or heterocyclic acids or aldehydes according to procedures known in the art, including 1) By condensation of a) o-phenylenediamine, b) aminophenols, c) thiophenols with salicylaldehydes followed by oxidation with Pb(OAc)₄ (Stephens et al., J. CHEM. SOC. 2971 (1949)].

2) By heating of o-aminothiophenols with salicylamides in DMSO (Delegiorgiev, DYES AND PIGMENTS 12, 243 (1990))

3) By polyphosphoric acid catalyzed condensation of carboxylic acid derivatives with o-amino, o-hydroxy or o-mercaptoaroyl amines (Hein et al., JACS 79, 427 (1957))

Table 5 lists some Schiffs bases and the color of their fluorescent precipitates. Schiffs bases are prepared by heating of an aromatic aldehyde with a substituted aniline in a suitable solvent such as EtOH or toluene (Kresze et al., Z. NATURFORSCHUNG 10B, 370 (1955) and Example 3).

TABLE 5

Schiffs Bases according to the formula:

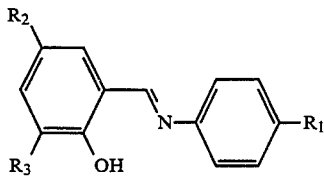

| | Schiffs base | $R_1$ | $R_2$ | $R_3$ | mp [°C.] | Yield [%] | Color[1] |
|---|---|---|---|---|---|---|---|
| 1d | 2-hydroxybenzylidene-p-dimethylaminophenyl imine | $NMe_2$ | H | H | 136–38 | 89 | o |
| 2d | 3,5-dichloro-2-hydroxy-benzylidene-4'-p-dimethylaminophenyl imine | $NMe_2$ | Cl | Cl | — | 72 | r |
| 3d | 2-hydroxy-5-nitrobenzylidene-p'-dimethylaminophenyl imine | $NMe_2$ | $NO_2$ | H | 212–14 | 99 | r |
| 4d | 5-chloro-2-hydroxy-benzylidene-4'-dimethylaminophenyl imine | $NMe_2$ | Cl | H | 188–90 | 84 | o |
| 5d | 3,5-dichloro-2-hydroxy-benzylidene-p-dimethylaminophenyl imine | OMe | Cl | Cl | 114–16 | 96 | o |

[1]Color of fluorescence: o = orange, r = red

Preparation of Fluorogenic Substrates

In certain instances, especially where BLOCK is incorporated to yield a simple aliphatic ether substrate for a cytochrome enzyme, it is preferable to incorporate BLOCK before formation of $X_{fl}$ (for instance see Example 10). Generally, however, the substrates of this invention are prepared by the following steps:

1) preparation of a suitable fluorophore such as those already mentioned above; and
2) reaction of the fluorophore with an appropriate form of a blocking reagent to form the substrate.

BLOCK is typically bonded to $X_{fl}$ by reaction of a reactive form of BLOCK with the hydroxyl group present in the unbound form of $X_n$ through the intermediacy of a reactive derivative of BLOCK that can subsequently be converted to BLOCK. For instance, phosphate is incorporated using a reactive form of phosphate such as phosphorous oxychloride in Example 7 or such as via phosphoramidite chemistry in Example 7. Sulfate is typically incorporated by reaction with chlorosulfonic acid as demonstrated in Example 6. Carboxylate esters are typically incorporated by reaction with an activated form of the acid (for instance anhydride, mixed anhydride, acid halide) as shown in Examples 8 and 9.

Glycosides are typically prepared by a modified Koenigs-Knorr methodology involving treatment of the unbound form of $X_{fl}$ with a soft acid catalyst (for instance silver carbonate), an activated protected carbohydrate (APC) derivative, and a nonnucleophilic base (for instance sym-collidine), under anhydrous conditions (FIG. 1). The APC will contain one or more sugars with an activating group at the anomeric position of the sugar to be attached to $X_{fl}$. Typically the APC is a halogenated sugar, where a halogen is the activating group at the anomeric position. Depending on the reaction conditions, the sugar(s) involved, or the anomeric isomer required, other activation groups at the anomeric position of the APC can be used, most commonly trichloroacetimidate, thiophenyl or acetate. This will result in the production of a nonfluorescent glycoside intermediate. After isolation of the protected glycoside intermediate, the protecting groups are removed from the protected glycoside, using processes appropriate to the protecting group(s) present. Synthesis of representative examples of the subject substrates that contain glycosides are given in Examples 4 and 5.

The following Tables 6–8 contain representative phosphate substrates. Although all of the substrates in Tables 6–8 are phosphates, any suitable blocking group previously described could be substituted to prepare the same range of substrates for detecting or analyzing a particular enzyme. For example, Table 9 illustrates some of the same substrates that can be made as glycosides. The number of phosphate substrates described herein are merely representative of some of the choices available for detection of phosphatase enzymes. The range of choices are meant to illustrate, and not to limit the range of possible fluorogenic substrates with a variety of properties. Any of the described fluorophores can be used to prepare a substrate for a wide range of enzymes. By appropriate choice of fluorophores, blocking groups, and substituents, in particular, the substrate can be tailored to give desired properties of reactivity, solubility, fluorescence intensity and wavelengths, and product photostability. Table 6 gives a summary of the synthesis of some quinazolinone phosphates prepared as in Example 7. Table 7 gives a summary of the synthesis of some benzoquinazolinone phosphates prepared as in Example 7. Table 8 gives a summary of the synthesis of some benzothiazole phosphates.

TABLE 6

2-phosphoryloxyphenyl-4-(3H)-quinazolinones (disodium salts) according to the formula:

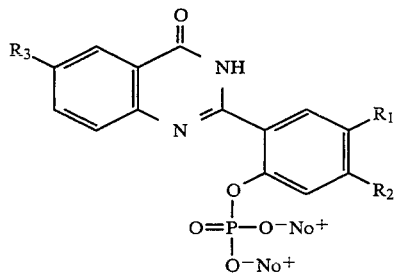

| # | 4-(3H)-quinazolinone-2'-phosphates (disodium salts) | $R_1$ | $R_2$ | $R_3$ | Yield [%] | Yield of intermediate di-t-butyl ester [%] | $R_f$(phosphate) i-PrOH/NH₃/H₂O 70/10/20 |
|---|---|---|---|---|---|---|---|
| 1e | 2-phenyl | H | H | H | 76 | 99 | 0.38 |
| 2e | 2-(5'-methoxyphenyl) | H | H | OCH₃ | 86 | 90 | 0.36 |
| 3e | 2-(4'-methoxyphenyl) | H | OCH₃ | H | 89 | 99 | 0.36 |
| 4e | 2-(5'-nitrophenyl)-6-nitro | NO₂ | H | NO₂ | 84 | 95 | 0.52 |
| 5e | 2-(5'-methoxyphenyl)-6-chloro | Cl | H | OCH₃ | 90 | 92 | 0.37 |
| 6e | 2-phenyl-6-nitro | NO₂ | H | H | 92 | 96 | — |
| 7e | 2-(5'-chlorophenyl)-6-nitro | NO₂ | H | Cl | 83 | 89 | — |
| 8e | 2-(5'-chlorophenyl)-6-chloro- | Cl | H | Cl | 82 | 86 | 0.39 |
| 9e | 2-(5'-chlorophenyl) | H | H | Cl | 95 | 96 | 0.38 |

TABLE 7

Benzo 4-(3H)-quinazolinone-2¹-phosphates (disodium salt) according to the formula:

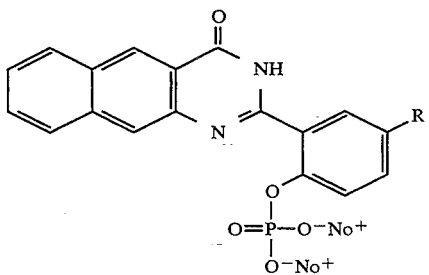

| # | Benzo-4-(3H)-quinazolinone-2'-phosphate (disodium salt) | R | Yield [%] | Yield of intermediate di-t-butyl ester [%] | $R_f$(phosphate) i-PrOH/NH₃/H₂O 70/10/20 |
|---|---|---|---|---|---|
| 1f | 2-phenyl | H | 87 | 91 | 0.36 |
| 2f | 2-(5'-chlorophenyl) | Cl | 90 | 92 | 0.37 |

TABLE 8

Benzothiazole phosphates (disodium salts) according to the formula:

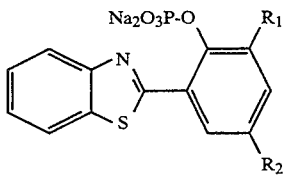

| # | Benzothiazole-2'-phosphate (disodium salt) | $R_1$ | $R_2$ | Yield [%] | Yield of intermediate di-t-butyl ester [%] | $R_f$(phosphate) i-PrOH/NH₃/H₂O 70/10/20 |
|---|---|---|---|---|---|---|
| 1g | 2-phenyl | H | H | 96 | 98 | 0.37 |
| 2g | 2-(5'-methoxyphenyl) | H | OCH₃ | 79 | — | 0.39 |
| 3g | 2-(3',5'-dichlorophenyl) | Cl | Cl | 71 | — | 0.38 |

TABLE 9

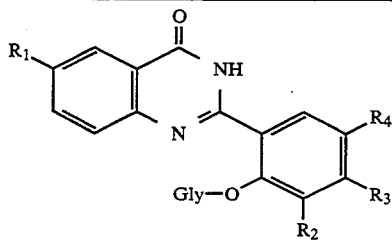

4-(3H)-Quinazolinone-Glycosides

| # | 4-(3H)-Quinazolinone-Glycosides | $R_1$ | $R_2$ | $R_3$ | $R_4$ |
|---|---|---|---|---|---|
| 1h | 2-(2'-galactopyranosyl-oxyphenyl)- | H | H | H | H |
| 2h | 2-(5'-chloro-2'-galactopyranosyloxyphenyl)-6-chloro- | Cl | H | H | Cl |
| 3h | 2-(2'-galactopyranosyloxy-5'-methoxyphenyl)- | H | H | H | OCH$_3$ |
| 4h | 2-(2'-glucopyranosidurano-syloxyphenyl)- | H | H | H | H |
| 5h | 2-(2'-cellobiosyloxyphenyl)- | H | H | H | H |
| 6h | 2-(2'-glucopyranosyl-oxyphenyl)- | H | H | H | H |
| 7h | 2-(2'-mannopyranosyl-oxyphenyl)- | H | H | H | H |
| 8h | 2-(2'-Fucopyranosyl-oxyphenyl)- | H | H | H | H |

Properties of Preferred Substrates

As compared with other synthetic substrates, the fluorogenic precipitating substrates described in this invention normally have high enzymatic turnover rates and moderate affinities for the enzymes. Turnover rates of the substrates can be determined as in Example 10 and expressed as micromoles of product per minute per milligram protein ($k_2$, in units of $\mu\text{mol·min}^{-1}\cdot\text{mg}^{-1}$). The affinity of the substrate is determined by its dissociation constant, $K_M$, in millimolar units. The enzymes can bind to and catalyze conversion of the soluble substrates into detectable reaction products that are apparently less soluble and will precipitate in aqueous solutions. The preferred detectable reaction products are fluorescent precipitates. The precipitation, however, and thus fluorescence, depends on the reaction product concentration or the initial substrate concentration used, as well as the ionization state of the product's phenol group. There are two parameters determining the precipitation, i.e. critical concentration ($M_c$) and pH dependence ($pK_a$). A method for determination of these parameters is given in Example 11. Table 10 gives the relevant parameters for the enzymatic reaction and precipitation of quinazolinone-based alkaline phosphatase substrates.

TABLE 10

Characterization of quinazolinone-based substrates for phosphatase enzymes

| Quinazolinone Phosphates | $k_2$ ($\mu$mol/min · mg) | $K_M$ (mM) | $M_c^{(1)}$ (mM) | $pK_a^{(2)}$ |
|---|---|---|---|---|
| 2-phenyl | 188.81 | 5.00 | 1.5 | 13.5 |
| 2-(5'-methoxy-phenyl) | N/D | N/D | 0.8 | 8.8 |
| 2-(4'-methoxy-phenyl) | N/D | N/D | 2.5 | 8.8 |
| 2-(5'-methoxy-phenyl)-6-chloro | N/D | N/D | 1.2 | 10.5 |
| 2-phenyl-6-nitro | 150.66 | 9.1 | 1.2 | 8.8 |
| 2-(5'-chlorophenyl) | N/D | N/D | 0.4 | 8.5 |
| 2-(5'-chlorophenyl)- | 618.60 | 75.0 | 0.1 | 10.5 |
| 6-chloro 2-(3',5'-dimethoxy-phenyl) | 215.60 | 10.8 | 0.3 | 11.0 |

The assays which use the substrates of this invention are rapid and highly sensitive. Due to the high $pK_a$-values of the fluorophores ($pK_a \geq 8.5$) and the fact that the protonated neutral form of the dye is the fluorescent species, these assays can be carried out within a relatively wide pH-range that is near or below the $pK_a$ of the phenolic group. Formation of the fluorescent precipitate does not require addition of any particular additives beyond the enzyme, substrate and appropriate buffered medium to facilitate the enzymatic reaction. Absorbance and fluorescence of the precipitate is pH insensitive and exhibits a maximal intensity that can be detected at a wavelength that is greater than about 100 nm longer than the longest wavelength for maximal excitation of the precipitate. This appreciable Stokes shift has the significant advantage of reducing background fluorescence in the sample.

Detection of Enzymatic Activity Using the Precipitating Substrates

The present invention can be used to qualitatively or quantitatively detect the activity of any enzyme that is capable of cleaving the blocking group from the remainder of the molecule to yield a fluorescent phenolic detection product. The enzyme may act by hydrolysis or by a nonhydrolytic mechanism, either mechanism resulting in formation of the same phenolic detection product. The enzyme may be active in a living or non-living system.

The method for detecting the activity of an enzyme includes the following steps:

A) combining a sample suspected of containing the enzyme with a substrate of the type described above, under conditions suitable for the formation of a visible precipitate; and B) qualitatively or quantitatively evaluating the precipitate.

The substrate may be combined with the sample by any means that facilitates contact between the enzyme and the substrate. The contact can occur through simple mixing, as in the case where the sample is a solution. The solution can vary from one of purified enzymes to cell extracts to unfiltered biological fluids such as urine, cerebral spinal fluid, blood, lymph fluids, tissue homogenate, mucous, saliva, stool, physiological secretions, etc. In some cases it is desirable to separate the enzyme from a mixture of biomolecules or fluids in the solution prior to combination with the substrate. Numerous techniques exist for separation and purification of proteins, including enzymes, from generally crude mixtures with other proteins or other biological molecules. These include such means as electrophoretic techniques and liquid, size-exclusion, ion-exchange, affinity and adsorption chromatography. These share the common feature that the products are collected in fractions that are characteristic of the given protein.

Following the separation or purification technique, the substrate may be added to the solution directly or may contact the solution on an inert matrix such as a blot or gel, a testing strip, or any other solid or semi-solid surface, for example where only a simple and visible demonstration of the enzymatic activity is desired. Example 12 provides a typical procedure for detecting and quantitating the enzymatic activity in solution and after adsorption onto a synthetic membrane. Example 13 provides a means for detecting this enzyme activity following separation by a chromatographic technique. Example 14 provides a means for detecting this enzymatic activity following separation of a mixture of proteins by an electrophoretic technique. Any inert matrix used to separate the sample can be used to detect enzyme activity by observing the fluorescent deposit on the inert matrix. The enzyme facilitates precipitation of high local concentrations of the enzymatic products where it is immobilized on the inert matrix.

The immobilizing matrix on which substrate and sample come in contact may be a membrane. Enzymes from various biological sources can be immobilized on nylon, nitrocellulose or other membranes without appreciable loss of enzymatic activity. A solution of a suitable fluorogenic precipitating substrate is then added to the membrane supports. Using suitable illumination, such as provided by an ultraviolet lamp, the immobilized enzymes can be visualized in a "dot blot" as fluorescent spots on the membrane (see Example 12). This detection methodology is convenient, inexpensive and very sensitive. A mass of 0.5 ng alkaline phosphatase can produce a dense and bright fluorescent spot on the membranes that is clearly visible by eye when illuminated by a conventional UV lamp. Such detection techniques requiring little or no elaborate instrumentation are particularly desirable in clinical diagnosis. For example, determining the serum level of alkaline phosphatase activity on the membrane supports as described above could be of help in diagnosing Paget's disease [Farley, et al. J. BIOL. CHEM. 225, 4680 (1980)].

Another use of the fluorogenic precipitating substrates with a solid matrix is in analyzing isoenzymes of a particular enzyme. This application may be particularly useful in clinical diagnosis where it is known, for example, that the hepatic isoenzyme spectrum of alkaline phosphatase changes in response to liver disease [Winkelman, et al., AM. J. CLIN. PATHOL. 57, 625, (1972)]. The isoenzyme spectrum can be routinely obtained by incubating the electrophoretic gel of a human hepatic sample run under nondenaturing conditions (as in Example 14) with a fluorogenic precipitating substrate for phosphatase, since the small substrate molecule can readily penetrate into the gel medium to react and form a highly fluorescent precipitate. It is understood that the subject phosphatase substrates will also be useful for analysis of acid phosphatase or total phosphatase isoenzymes, and are not limited to detecting alkaline phosphatase isoenzymes. Other isoenzyme spectra, e.g. for cytochrome enzymes, may be similarly evaluated using samples from different organisms or different tissues from the same organism.

The subject substrates may also be combined with samples that are or contain whole cells. The fluorogenic precipitating substrates readily enter live cells and react with endogenous activities of particular enzymes such as β-galactosidase and alkaline phosphatase under normal physiological conditions. The substrates can also be used for staining the endogenous activities of alkaline phosphatase in a cell that is fixed and treated with routine histochemical or cytochemical procedures. Although most of the substrates have been found to enter the cells by passive diffusion, the substrates may enter the cells by any technique that is suitable for transporting the substrate across cell membranes with minimal disruption of the viability of the cell and integrity of cell membranes. Examples of suitable processes include action of chemical agents such as detergents, enzymes or adenosine triphosphate; receptor- or transport protein-mediated uptake; pore-forming proteins; microinjection; electroporation; hypo-osmotic shock; or minimal physical disruption such as scrape loading or bombardment with solid particles coated with or in the presence of the substrate.

The enzyme being evaluated may be present in the cell either as the result of expression of an endogenous gene or of a foreign gene introduced by means of viral transfection or genetic manipulation (see Example 15). For example, the gene that encodes β-galactosidase is often fused with other genes or with genomic regulatory elements. The resulting DNA constructs are then introduced into the cell of interest, and β-galactosidase expression is assayed to ensure proper gene expression. Using this technique, one can investigate expression efficiency of the encoding gene, which may be affected by promoter and/or repressor manipulations. The nontoxic and sensitive detection of the enzyme activities in live cells is very useful in testing the success of gene fusion, particularly when it is desirable to reuse the tested cells. For example, β-galactosidase activity resulting from lacZ gene expression has been used to detect the incorporation of lacZ gene fusion constructs in cells that lack endogenous β-galactosidase activity. The fluorogenic precipitating substrates for β-galactosidase release a well-retained fluorescent precipitate in lacZ positive cells and allow easy identification and further sorting of the positive cells. The substrates can also be used to probe cell populations or inert samples for cells expressing the enzyme, such as in the determination of bacterial contamination of biological samples. Also the examination of endogenous enzyme activity in tissue or cells by the corresponding fluorescent substrates is of significance in gaining information about the histological distribution of the enzyme, developmental stage-specific expression of the enzyme, or cancer related expression of the enzyme. In either live cells or fixed cells, the enzyme activities are reflected by the fluorescent precipitates at the activity sites.

The substrate is combined with the sample under conditions suitable for the formation of the precipitate. Preferably the sample is in an aqueous buffer at a pH greater than about 2 and less than about 11, more preferably at a pH between about 5–8. The concentration of the substrate must be sufficient to give a detectable reaction product. The concentration sufficient to give a detectable reaction is related to pH, with a lower concentration required at a lower pH. A concentration of substrate between about 0.1 mM and 1 mM is sufficient for formation of precipitate at a pH of about 8.5 or lower. A concentration of substrate greater than about 5 mM is sufficient for formation of a precipitate even above pH 11. At pH greater than about 8.5, a concentration of substrate greater than about 2.0 mM is necessary to form a precipitate in solution. Where the enzyme is at a fixed location, a lower concentration of the substrate may result in formation of a visible precipitate. Typically, the precipitate forms within several minutes after interaction of the substrate with the enzyme. Usually, optimal precipitation is obtained within about 15 minutes to about one hour.

To facilitate the detection of the visible precipitate, the excitation or emission properties of the precipitate are utilized. For example, the precipitate (H—O—$X_{fl}$) is excited by a light source capable of producing light at or near the wavelength of maximum absorption of the fluorescent product, such as an ultraviolet or visible lamp, an arc lamp, a laser, or even sunlight. Preferably the fluorescent precipitate is excited at a wavelength equal to or greater than about 300 nm, more preferably equal to or greater than about 340 nm. The fluorescence of the precipitate is detected qualitatively or quantitatively by detection of the resultant light emission at a wavelength of greater than about 400 nm, preferably greater than about 450 nm. The emission is detected by means that include visible inspection, photographic film, or use of instrumentation such as fluorometers, quantum counters, plate readers, microscopes and flow cytometers, or by means for amplifying the signal such as a photomultiplier.

Figure 2A:
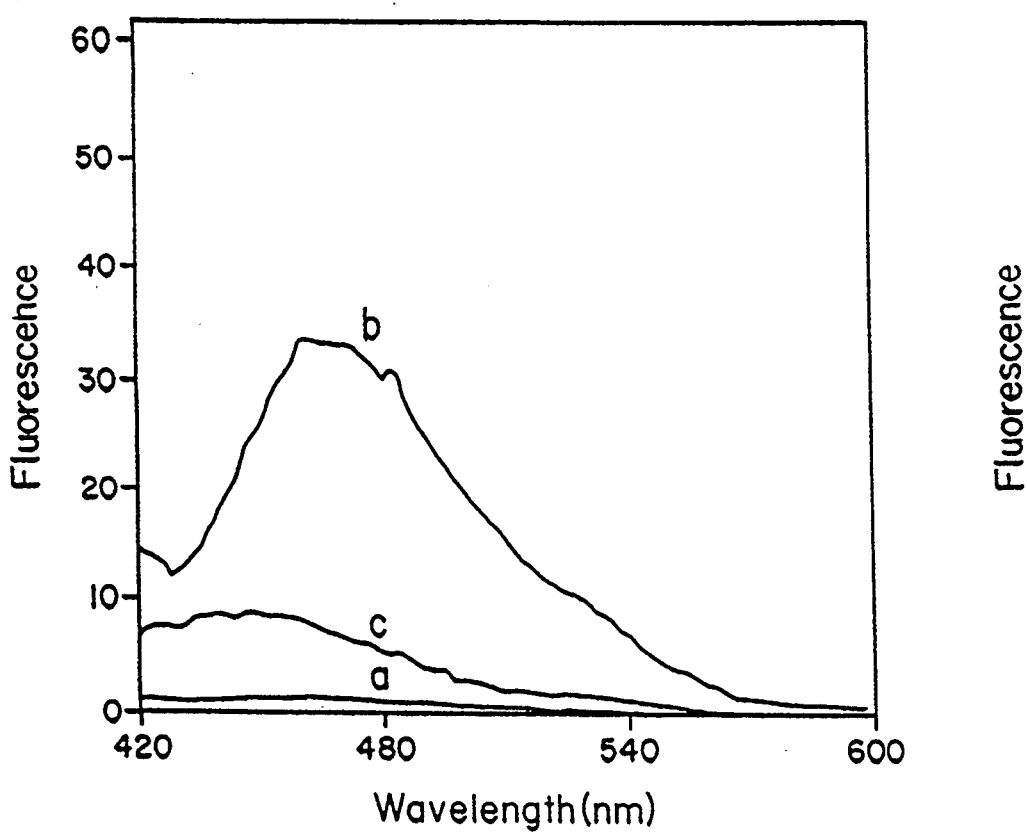
FIGS. 2A–2E: Characterization of the fluorogenic precipitating substrates.
Figure 2B:
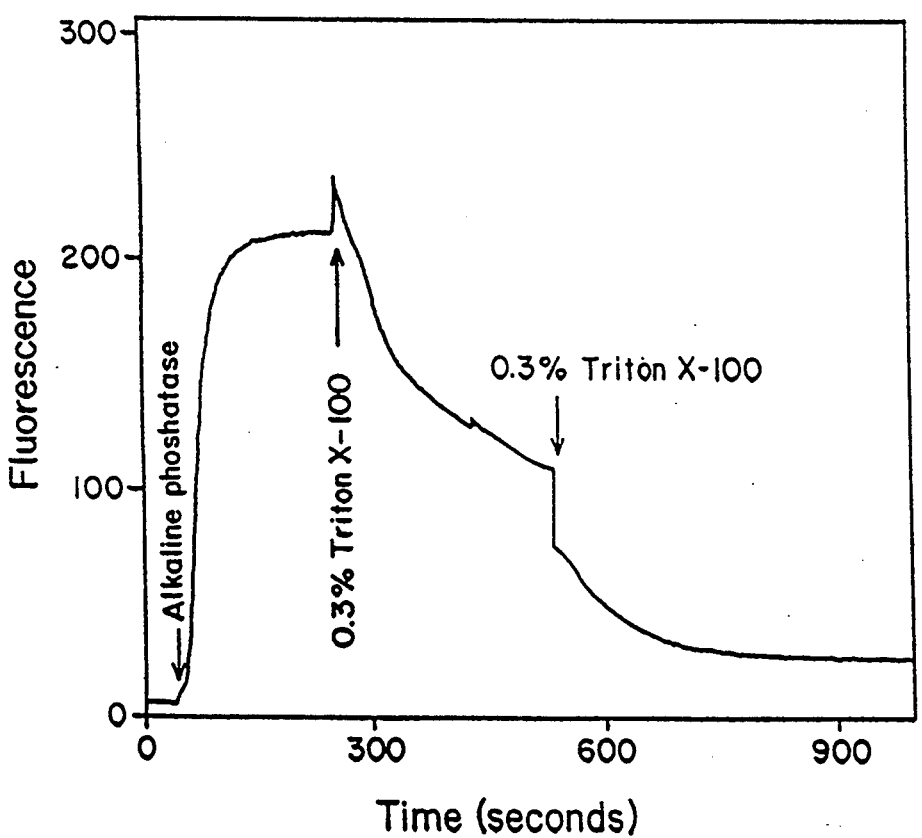
Figure 2C:
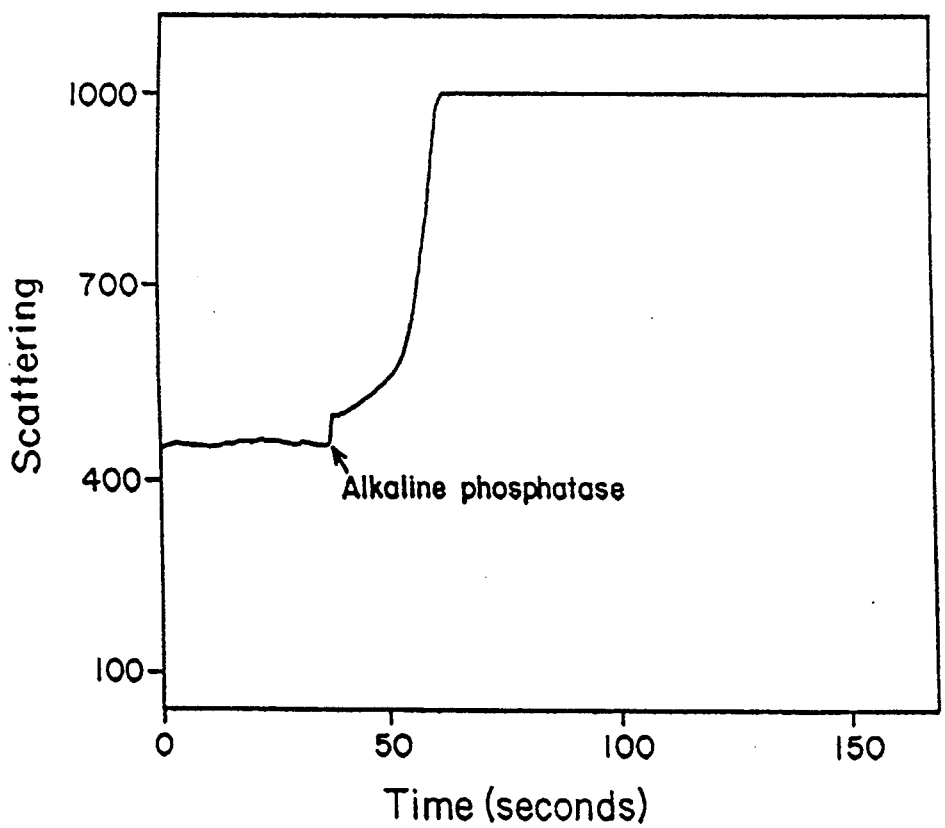
Figure 2D:
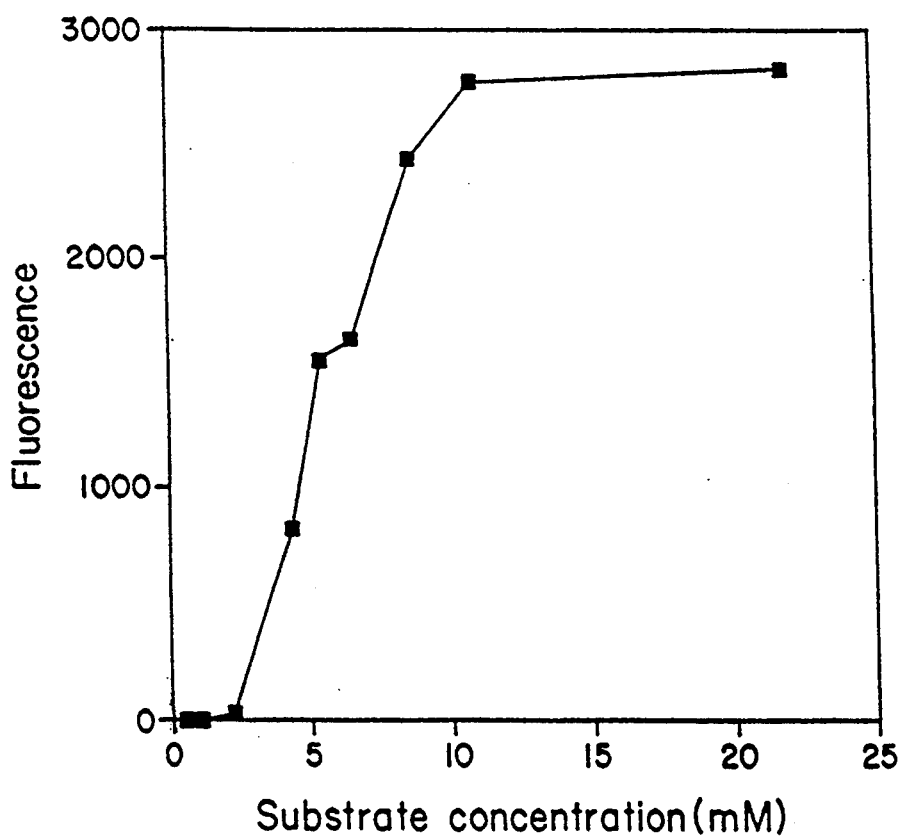
Figure 2E:
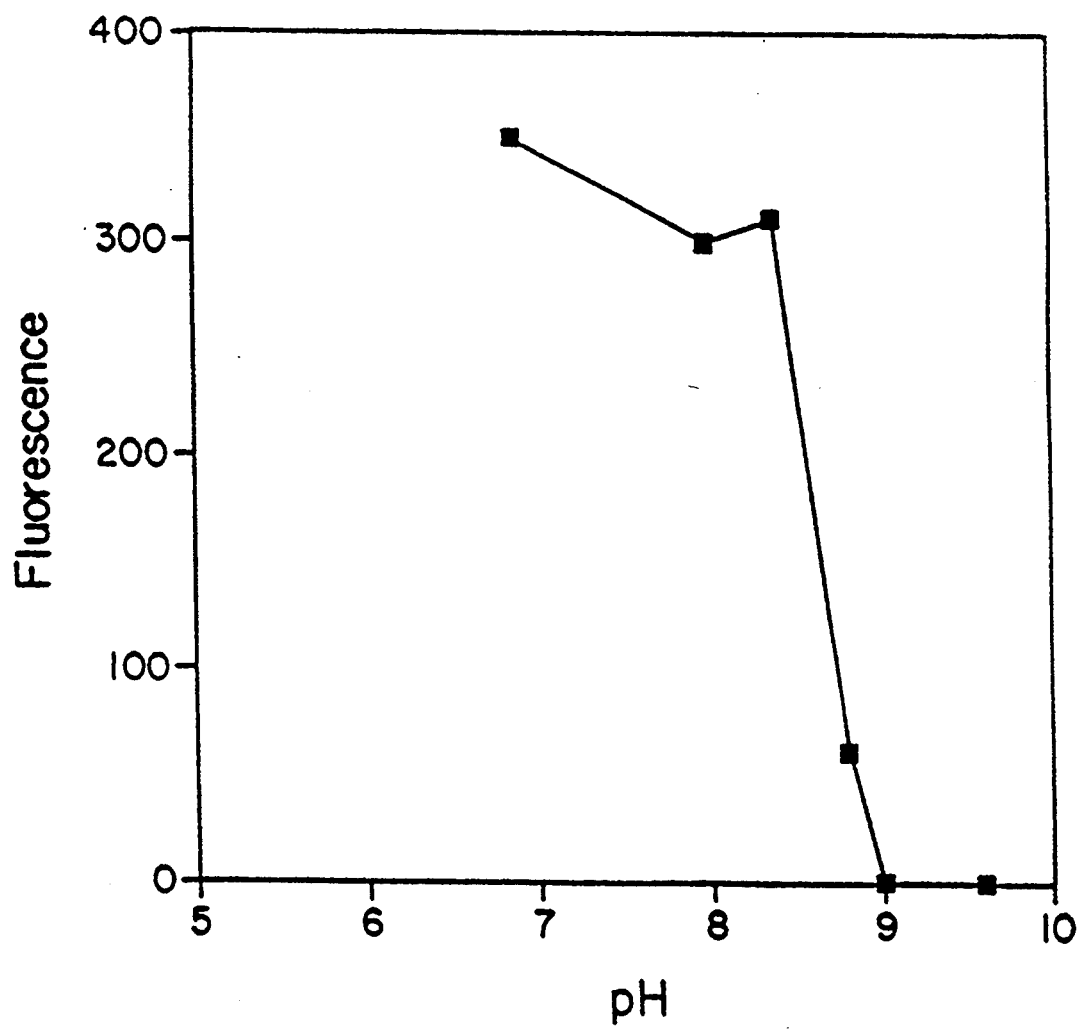

Identification and quantitation of the activity of enzymes from various sources and in various applications can be sensitively, specifically and yet versatilely performed with the use of the fluorogenic precipitating substrates (see for instance Examples 12, 13 and 14). This sensitivity and specificity is based on the high turnover rate of the substrates, dense fluorescence and high photostability of precipitated products and vast increase in the turbidity of the assay systems. For example, in 10 minutes, an activity equivalent to 10 ng of purified alkaline phosphatase can be easily detected by the fluorescence resulting from the hydrolysis of a quinazolinone phosphate that is measured in a cuvette and a fluorometer. The substrate hydrolysis also causes a sharp increase of the sample's turbidity (FIG. 2C). Thus the scattering measurement in a fluorometer or a spectrophotometer can give additional and affirmative information about the specific presence of the enzyme and yet provide an even more sensitive means for tracing alkaline phosphatase in quantities less than 1 ng. High enzymatic activities may be directly observed by eye as a turbid precipitate appearing in the enzymatic reaction. The co-measurement of fluorescence and turbidity can help ensure a double identification of the enzymes. A fluorescence plate reader utilizing a front-face measurement geometry is found to be very suitable for measuring a sample of high turbidity that results from either the sample itself or from precipitation during the enzymatic reaction (Example 12). The fluorogenic precipitating substrates in this invention can therefore be used for fast and automatic detection or screening of target enzymes isolated from many sources.

Detecting Activity of Enzymes as Conjugates

The substrates may be used in conjunction with enzyme conjugates to localize cellular receptors; to probe gels and blots; to localize hybridization probes; or to probe cells and tissues that do not express the enzyme, for example, by enzyme-linked immunosorbent assay (ELISA), or enzyme-mediated histochemistry or cytochemistry, or other enzyme-mediated techniques. Enzyme-mediated techniques take advantage of the attraction between specific binding pairs to detect a variety of analytes. Examples of specific binding pairs are listed in Table 11.

TABLE 11

| REPRESENTATIVE SPECIFIC BINDING PAIRS | |
|---|---|
| antigen | antibody |
| biotin | avidin (or streptavidin) |
| IgG≠ | protein A or protein G |
| drug receptor | drug |
| toxin receptor | toxin |
| carbohydrate | lectin |
| peptide receptor | peptide |
| protein receptor | protein |
| carbohydrate receptor | carbohydrate |
| DNA (RNA) | aDNA (aRNA)* |

≠IgG is an immunoglobulin.
*aDNA and aRNA are the antisense (complementary) strands used for hybridization In general, an enzyme-mediated technique uses an enzyme attached to one member of a specific binding pair or series of specific binding pairs as a reagent to detect the complementary member of the pair or series of pairs. In the simplest case, only the members of one specific binding pair are used. One member of the specific binding pair is the analyte, i.e. the substance of analytical interest. An enzyme is attached to the other (complementary) member of the pair, forming a complementary conjugate. The complementary conjugate attaches to its complementary analyte to form a complementary binding complex. Alternatively, multiple specific binding pairs may be sequentially linked to the analyte, the complementary conjugate, or to both, resulting in a series of specific binding pairs interposed between the analyte and the detectable enzyme of the complementary conjugate incorporated in the specific binding complex. Table 12 shows the representative examples of specific binding complexes with and without additional specific binding pairs interposed between the complementary conjugate and the analyte.

TABLE 12

| REPRESENTATIVE SPECIFIC BINDING COMPLEXES | | |
|---|---|---|
| ANALYTE | ADDITIONAL PAIRS | COMPLEMENTARY CONJUGATE |
| DNA | aDNA–biotin  avidin | biotin–enzyme |
| DNA | aDNA–antigen  antibody–biotin  avidin | biotin–enzyme |
| DNA | | aDNA–enzyme |
| DNA | aDNA–biotin | avidin–enzyme |
| DNA | aDNA–hapten* | anti-hapten–enzyme |
| RNA | aRNA–hapten* | anti-hapten–enzyme |
| RNA | aDNA–biotin | avidin–enzyme |
| antigen | mouse antibody  anti-mouse–biotin | avidin–enzyme |
| antigen | mouse antibody  anti-mouse | mouse anti-enzyme . enzyme |
| antigen | | antibody–enzyme |
| antigen | antibody–hapten* | anti-hapten–enzyme |
| carbohydrate | lectin–biotin | avidin–enzyme |
| receptor ≠ | ligand–biotin | anti-biotin–enzyme |

TABLE 12-continued
REPRESENTATIVE SPECIFIC BINDING COMPLEXES

| ANALYTE | ADDITIONAL PAIRS | COMPLEMENTARY CONJUGATE |
|---|---|---|
| IgG | protein A--hapten* | anti-hapten--enzyme |

*a hapten is any group for which there is an antibody, typically low molecular weight molecules such as drugs, dyes, and aromatic molecules
‡for instance a drug receptor, a toxin receptor, peptide receptor, protein receptor or carbohydrate receptor
--is a covalent bond between two reagents; all other bonds are noncovalent At one end of the specific binding complex is an analyte. The analyte is any molecular species for which there exists a complementary agent that forms a specific binding pair. Typically, the analyte is a component of a biological cell or has been isolated from a biological cell. The analyte may be any of the agents listed in Table 11 above. If the analyte is part of or derived from a biological cell, the cell may be of animal, plant, bacteria or yeast origin. The cells may be living, or they may be dead. The cells may be isolated, in tissue, in vivo or in vitro. The analyte may be derived from a biological cell by any process that permits separation from the cell such as by disruption, extraction, precipitation, adsorption, or chromatographic or electrophoretic separation.

At the other end of the specific binding complex is the complementary conjugate incorporating the enzyme. Attachment of the enzyme to the complementary conjugate is typically by a covalent bond. Alternately, the high affinity of antibodies may be exploited, using an anti-enzyme-enzyme interaction to hold the enzyme to the specific binding complex. Numerous methods and reagents exist for making the covalent bond such as glutaraldehyde or succinimidyl 2-pyridyldithiopropionate (SPDP)[Biochem J 173, 723 (1976)]. Alternatively it is convenient to couple biotinylated enzymes to biotinylated analytes (or to biotinylated intermediates that can form a second specific binding pair with the analyte) via the intermediacy of avidin or streptavidin since the latter reagents have four biotin binding sites each (see Example 19). Many ligands can be conjugated with biotin without loss of their affinity for the complementary members of their specific binding pairs. Glycosidase and phosphatase enzymes are frequently chosen as label enzymes because of their high turnover rate, low cost and unique capacity to detect with high sensitivity biological analytes in samples that have no enzymatic activity. The enzyme incorporated in the specific binding complex interacts with the subject substrate to remove BLOCK and form a visible precipitate. Detection of the interaction of the substrate with the enzyme-conjugated specific binding complex, and thus the presence of the analyte, is by fluorescence, light scattering, or visible appearance. Unlike virtually all existing reagents for detection of this interaction, removal of BLOCK results in formation of a detectable fluorescent precipitate precisely at the site of the interaction. A sample thought to contain a specific binding complex in association with a particular analyte can be contacted with the appropriate substrate in any of the ways previously described. Similarly, following the formation of the precipitate, the desired qualitative and quantitative measurements are likewise obtained using procedures comparable to those previously described.

These unique substrates are useful for enzyme-mediated methods used in standard blotting techniques for identifying and semi-quantitating specific species of proteins, RNAs or DNAs. For example, the dot blot experiments include immobilization of proteins or nucleic acids on membranes followed by specific detection by antibody-enzyme or avidin-enzyme conjugates along with the fluorogenic precipitating substrates (Examples 12 and 16). For the nucleic acid dot blot, the immobilized nucleic acid is allowed to hybridize with biotin-labeled complementary DNA or RNA probes before applying the enzyme-avidin or -streptavidin conjugates. The detection sensitivity of the dot blot using the subject substrates is equal to or even greater than those using the colored precipitating substrates, i.e. 5-bromo-4-chloro-3-indolyl phosphate for phosphatase, 5-bromo-4-chloro-3-indolyl galactoside (X-gal) for galactosidase and 5-bromo-4-chloro-3-indolyl sulfate for sulfatase.

Western, Northern, and Southern blots, however, are designed to specifically recognize the proteins and nucleic acids following electrophoretic separation. The separated bands are then typically transferred to membrane supports that are suitable for subsequent binding of protein-specific antibodies or DNA or RNA sequences, as well as for reaction with the fluorogenic precipitating substrates. The resolution demonstrated on the transferred membranes by use of the precipitating substrates is comparable to that obtained by use of chromophoric precipitating substrates, chemiluminescent substrates and radioisotope labeling.

The fluorescent substrates in this invention provide a unique approach to improving histochemical or cytochemical detections. As stated previously, these techniques can be used to probe for an infinite number of antigens and DNA or RNA sequences. Since most cells or tissues have little or no autofluorescence, the signal, i.e. the fluorescent precipitate resulting from an enzyme reaction associated with the analytes being detected, has an overwhelming contrast over the dark background, thus allowing very sensitive detection of a relatively small number of analyte molecules. Furthermore, the unusually large Stokes shift found in most of the subject dyes (frequently over 100 nm, often over 150 nm) further enhances resolution of the signal fluorescence over the background.

Fluorescently labeled antibodies or ligands have frequently been used to stain cell-surface receptors. The fluorescent antibody usually has higher detection sensitivity than the fluorescently labeled endogenous ligand, since an antibody can be conjugated with relatively more fluorophores without loss of biological activity. Moreover, the enzyme-mediated deposition of numerous fluorescent molecules further enhances the signal. This is shown in concanavalin A (Con A) receptor visualization in NIH 3T3 cells (Example 17). Using biotinylated Con A, a streptavidin-alkaline phosphatase conjugate and a fluorogenic precipitating substrate for alkaline phosphatase, the Con A receptors can be observed under a conventional fluorescence microscopy as much brighter and more dense fluorescent spots than can be observed using common fluorescent Con A staining techniques. As another demonstration of the advantage of the precipitating substrates, epidermal growth factor (EGF) receptors present in human epidermoid carcinoma, A431 cells (Example 18), are difficult to visibly detect using EGF labeled with a single fluorophore, even though binding experiments indicate that these fluorescent EGFs have a high affinity for the receptors of A431 cells (the dissociation constant is about 2.5 nM). Raising the EGF concentration generally results in nonspecific staining that cannot be blocked by unlabeled EGF. Certain cell receptors are present in such low quantities that detection using even the most efficient fluorophores such as the phycobiliproteins is not possible. However, the EGF receptors in A431 cells can be visualized as dense, bright and punctate fluorescent stains by use of biotin EGF, streptavidin-alkaline phosphatase, a fluorogenic precipitating substrate for alkaline phosphatase with detection by conventional fluorescent microscopy. This staining method is specific for the EGF receptor since staining can be totally blocked by unlabeled EGF.

It is obvious that, for histochemical and cytochemical applications, a fluorogenic precipitating substrate is superior to a chromophoric precipitating substrate in terms of signal over noise, and is superior to labeling with radioactive isotopes in terms of both detection sensitivity and spatial resolution. This makes the fluorogenic precipitating substrates particularly useful for in situ hybridization for detecting the amount and distribution of a specific sequence of RNA or DNA in a single cell, either from the cell genome or from an invasion of a foreign gene such as a virus, bacterium or fungus (Example 20). Modern DNA synthesis has permitted an automatic and routine preparation and labeling of an oligonucleotide with lengths up to about 100 bases. The fluorogenic precipitating substrates in this invention, can be used to detect enzyme-conjugates bound to these short, sparsely labeled oligonucleotide probes. The fluorescent precipitate resulting from few or even single enzyme conjugates that are associated with a probe as short as 20 bases may be visible by conventional fluorescence microscopy. The improved detectability of the precipitated products and their associated high photostability invariably enhance the signal well above that obtainable with direct fluorophore conjugates of avidins or antibodies. The substrates in this invention represent an important advance in in situ hybridization for mRNAs, viruses as well as genomic DNA.

Modern flow cytometry has been a powerful tool for identifying and sorting cells (see for instance the book *Flow Cytometry and Sorting*, Melamed, Lindmo and Mwendelsohn, Wiley-Liss (1990) for background and applications of flow cytometry). The diverse applications of flow cytometry in cell biology and clinical diagnosis greatly rely on development of fluorescent dyes and dye-labeling techniques. In most cases, fluorescently labeled antibodies recognizing cellular analytes, particularly cell-surface antigens or receptors, are successfully used to analyze and sort cell populations on a single-cell basis. The enzyme-amplification technique using the substrates described in this invention provides a higher measurable signal, and therefore permits more sensitive cell analysis and cell sorting by a flow cytometer. For example, Con A or EGF receptors on a cell membrane can be quantitated and sorted by use of a biotin-labeled Con A or biotin EGF, a streptavidin-enzyme conjugate and a corresponding fluorogenic precipitating substrate. Histochemical studies suggest that the fluorescent precipitates may irreversibly deposit on cell membranous or cytoplasmic structures. The fluorescent precipitate will permit a lower detection limit of cell-surface receptors, thus allowing more precise cell analysis and sorting based on the numbers of receptors present on any given cell. The precipitate also provides a detectable scattering parameter in addition to the fluorescence. The flow cytometer's facile use of multiple parameters allow the characterization of an analyte from diverse aspects. Therefore the double examination of the fluorescence and the scattering rendered by the fluorogenic precipitating substrates may facilitate the collection of more complete and useful information about cellular analytes using a flow cytometer. Similarly, cells in a population can be distinguished and sorted by the endogenous activities of glycosidase, phosphatase, sulfatase, guanidinobenzoatase, esterase, cytochrome oxidase and other enzymes that liberate a fluorescent precipitate from one of the subject substrates in this invention as analyzed in the flow cytometer.

The following examples are included by way of illustration and not by way of limitation.

EXAMPLE 1: SYNTHESIS OF A QUINAZOLINONE DYE:

Synthesis of 2-(2'-hydroxyphenyl)-4-(3H)-quinazolinone (1a). Equimolar amounts of anthranilamide (1.3 g, 10 mmole) and salicylamide (1.2 g, 10 mmole) are suspended in 15 mL MeOH and refluxed for 30 minutes. After cooling of the reaction mixture to 20° C. the orange product is isolated and washed with MeOH. Yield: 2.2 g (94%). This product is suspended in EtOH and refluxed in the presence of catalytic amounts of p-toluenesulfonic acid (TsOH) for 1 hour and the formed colorless dihydroquinazolinone compound is suction filtered. Yield: 1.8 g (83%). The dihydroquinazolinone is suspended in MeOH and 1 mole equivalent of DDQ dissolved in MeOH is added. The suspension is refluxed for about 0.5 hour until the thin layer chromatogram (TLC) shows the disappearance of the blue fluorescent dihydro-compound. Yield: 1.56 g (85%); mp: 297°–298° C.

The 4-(3H)-quinazolinone derivatives such as those in Table I can be synthesized by using variations of the procedure described in this example.

EXAMPLE 2: SYNTHESIS OF A HETEROCYCLIC-CONTAINING QUINAZOLINONE DYE

Synthesis of 2-(2'-hydroxypyridyl)-4-(3H)-quinazolinone, (17a). To a stirred solution of 20 mmole of 3-hydroxypicolinamide (2.6 g) in 10 mL dimethylformamide is added 3.2 g (20 mmole) of isatoic anhydride. The mixture is heated to 80°–100° C. and then 5 mg of powdered potassium hydroxide is added. The mixture is kept at this temperature for 4 hours then cooled and the precipitate is isolated, washed with cold dimethylformamide and methanol. Yield: 2.2 g (46%); mp: 190°–192° C. Color of fluorescence: blue.

The 4-(3H)-quinazolinones and bis-4-(3H)-quinazolinones such as those in Table III can be prepared under conditions similar to those described in this example.

EXAMPLE 3: SYNTHESIS OF SCHIFF BASE DYES

Synthesis of 3,5-dichloro-2-hydroxybenzylidene-p-dimethylaminophenyl imine (2d) 0.95 g of 3,5-dichlorosalicylaldehyde and 1.05 g (10 mmole) of N,N-dimethyl-p-phenylenediamine, hydrochloride are dissolved in 15 mL of MeOH and the solution is refluxed for 1 hr. The resulting precipitate is filtered and washed with MeOH. Yield: 1.1 g (72%).

Under similar conditions Schiffs bases such as those in Table IV can be prepared by reaction of the appropriately substituted aromatic amine derivative with the appropriate aromatic aldehyde.

EXAMPLE 4: PREPARATION OF A SUBSTRATE CONTAINING A B-D-GALACTOPYRANOSIDE BLOCK AT THE HYDROXYL GROUP OF 2-HYDROXYPHENYL-4-(3H)-QUINAZOLONE. The following compound was prepared:

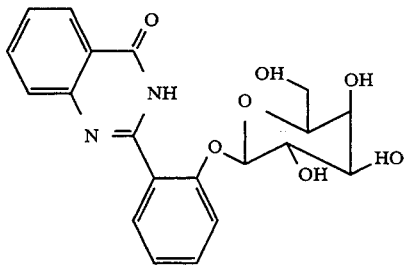

Synthesis of 2-(2-(β-D-galactopyranosyl)oxyphenyl)-4-(3H)-(quinazolone (1h). Under anhydrous conditions a mixture of 2-(2-hydroxyphenyl)-4-(3H)-quinazolone (1a)(10.0 g, 42 mmoles), activated 4 Å molecular sieves (2.0 g), and anhydrous methylene chloride (130 mL) is allowed to stir under dry $N_2$ for 1 hour at room temperature. Sym-collidine (6.6 mL, 50.4 mmoles) and silver carbonate (13.89 g, 50.4 mmoles) are then added and the mixture is stirred in the dark at room temperature for 30 minutes. 2,3,4,6-Tetra-O-acetyl α-D-galactosyl bromide (20.71 g, 50.4 mmoles) is added slowly with stirring and the mixture is stirred under dry $N_2$ in the dark at room temperature for 6 days. The mixture is filtered through a pad of diatomaceous earth and the residue is washed with chloroform (5×50 mL). The combined filtrates are extracted with 1M aqueous HCl solution (1×250 mL), saturated aqueous $NaHCO_3$ (1×250 mL), 0.1M aqueous $Na_2S_2O_3$ (1×250 mL), and water (1×250 mL). The organic layer is dried over anhydrous $MgSO_4$, evaporated, and dried in-vacuo to a light yellow solid (27.69 g, 116%). This crude intermediate is chromatographically separated on a column (8cm×32 cm, 700 g) of silica gel (35–70μ) and eluted by step-wise elution using 25% ethyl acetate 75% hexanes (2.0 L), followed by 33% ethyl acetate 67% hexanes (7.0 L). A total of 120×75 mL fractions are collected. Fractions 57–71 are shown by TLC to contain the desired product ($R_f$=0.14 when eluted with 33% ethyl acetate 67% hexanes). The protected glycoside is isolated by evaporation. The product is dried in vacuo (13.4 g, 56.1%). $^1$H NMR ($CDCl_3$)δ:8.45–8.42 (d, 1H); 8.18–8.15 (d, 1H); 7.8–8.0 (m, 2H); 7.56–7.61 (t, 1H); 7.39–7.44 (t, 1H); 7.05–7.08 (d, 1H); 6.97–7.00 (t, 1H); 6.40–6.43 (d, 1H); 5.71–5.77 (t, 1H); 5.56–5.70 (t, 1H); 5.29–5.33 (t, 1H); 4.34–4.38 (m, 1H); 4.17–4.26 (m, 2H); 2.23 (s, 3H); 2.06 (s, 3H); 1.99 (s, 3H); 1.90 (s, 3H).

A suspension of the above protected galactoside (568 mg, 1.00 mmoles) is prepared in 100 mL methanol and 30 mL methylene chloride. 250 μL of 1M $K_2CO_3$ (0.25 mmoles) is added and the mixture is stirred at room temperature for 1 hour. The reaction is determined by TLC to be complete (desired product at origin, starting material at $R_f$=0.55, decomposition product at $R_f$=0.84, 50% hexane, 50% ethyl acetate). The reaction is quenched by adding a mixture of 1 g IRC-50 strong acid and 1 g IRA-93 weak base Amberlite ™ ion exchange resins. After 10 minutes the resins are removed by vacuum filtration and washed with methanol. The filtrate is evaporated and dried in-vacuo (250 mg, 62%). This material is proven to be the desired product 1h by $^1$H NMR (DMSO-$d_6$)δ8.52 (d, 1H); 8.28 (m, 2H); 8.25 (d; 1H); 7.74 (t, 1H); 7.45 (m, 1H); 7.0 (m, 2H); 6.20 (d, 1H); 5.25 (m, 1H); 4.55 (m, 2H); 3.80 (m, 3H); 3.55 (m, 4H); 3.22 (m, 1H). Infrared minima at c$M^{-1}$ 751 (s); 766.94 (s) 1052.1 (s); 1080.0 (m); 1091.0 (m); 1490.5 (s); 1580.0 (s); 1583.1 (m); 3381.9 (s); 3389.7 (s); 3396.0 (s); 3402.2 (s); 3409.7 (s); 3416.7 (s); 3419.4 (s). Melting point/decomposition 140°–165° C. With the exception of products such as the glucuronide (Example 5) that require additional steps to remove protecting groups, glycosides derived from other carbohydrates are prepared similarly. Phenolic precursors other than 1a react similarly.

EXAMPLE 5: PREPARATION OF A SUBSTRATE HAVING A β-D-GLUCURONIC ACID BLOCK AT THE HYDROXYL GROUP OF 2-HYDROXYPHENYL-4-(3H)-QUINAZOLONE.

The following compound was prepared:

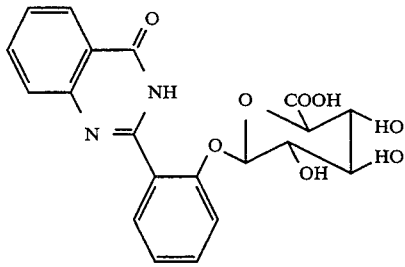

Synthesis of 2-(2-methyl-(2,3,4-tri-O-acetylβ-D-glucopyranosiduranyl)oxyphenyl)-4-(3H)-quinazolinone.

Under anhydrous conditions a mixture of 2-(2-hydroxyphenyl)-(3H)-quinazolone (1a)(1.95 g, 8.2 mmole), dry sym-collidine (1.31 mL, 9.9 mmole), silver carbonate (2.71 g, 9.8 mmole) and activated 3Å molecular sieve is allowed to stir in the dark, under an atmosphere of dry nitrogen gas, at room temperature for 1 hour. 2,3,4-Tri-O-acetyl-1-bromo α-D-glucopyranosiduronic acid, methyl ester (3.90 g, 9.8 mmole) is added slowly, and this mixture is allowed to continue stirring as above, protected from light, for 190 hours. The reaction mixture is filtered through a pad of diatomaceous earth, the precipitate is washed with chloroform (5×15 mL) and the combined filtrates are extracted with 1M aqueous HCl (1×100 mL), saturated aqueous $NaHCO_3$ solution (1×100 mL), saturated $Na_2CO_3$ solution (1×100 mL), 0.1M $Na_2S_2O_3$ solution (1×100 mL) and water (1×100 mL). The combined organic layers are dried over anhydrous $Na_2SO_4$, filtered, evaporated, and dried in vacuo to a tan foam (5.11 g). This sample is applied to a column of silica gel (300 g) and eluted by gradient elution using 3:1, 2:1 and finally 1:1 hexanes in ethyl acetate as eluent. Fractions containing the first UV absorbing product to elute from the column are combined and evaporated to a colorless foam (940 mg, 21%). TLC ($SiO_2$) (2:1 hexanes:ethyl acetate) $R_f$=0.24. $^1$H-NMR ($CDCl_3$)δ:8.4(d,1H); 8.1(d,1H); 7.95–7.87(m,2H); 7.6(dd,1H); 7.43(dd,1H); 7.08(d,1H); 6.97(t,1H); 6.61 (d,1H,H-1); 5.60–5.52(m,2H); 5.45(m, 1H); 4.45(d, 1H); 3.7(s,3H); 2.10(s,3H); 2.04(s,3H); 2.00(s,3H).

2-(2-O-δ-D-glucopyranosiduronate, methylester)-4-(3H)-quinazolone. A suspension of 2-(2-O-(2,3,4,-tri-O-acetyl β-D-glucopyranosiduronate, methyl ester)-4-(3H)-quinazolone (700 mg, 1.26 mmole) in anhydrous methanol (70 mL) is cooled to 0° C. in an ice-bath while under an atmosphere of dry nitrogen gas. A solution of freshly prepared sodium methoxide is added (1.4 mL 0.90M solution) and this mixture is stirred as above for 4.5 hours then at room temperature for 2 hours. The reaction is neutralized with washed, dry IRC 50 (H+) resin (pH 4), filtered, and evaporated to a tan powder which is dried in vacuo overnight (530 mg, 98%).

2-(2-O-β-D-glucopyranosiduronic acid)-4-(3H)-quinazolone(4H). A solution of 2-(2-O-βD-glucopyranosiduronate, methyl ester)-4-(3H)-quinazolone (100 mg, 0.23 mmole) in water (25 mL) is added to an ice-cold solution of 0.08M LiOH (4.36 mL, 1.5 equivalents) containing acetonitrile (10 mL) and stirred at 0° C. for 3 hours. Following neutralization with IRC 50 (H+) resin, the mixture is filtered, the methanol is evaporated under reduced pressure, and the aqueous solution is lyophilized to a tan powder (69 mg, 71%). An analytical sample can be purified by Sephadex LH 20 column chromatography (28×250 mm) and eluted with water. Fractions containing the second component to elute from the column are lyophilized to a colorless foam (27 mg from 50 mg applied to the column). TLC (SiO$_2$)(7:1:1:1 ethyl acetate:methanol:water:acetic acid) R$_f$=0.57. The $^1$H NMR in (d$_6$-DMSO) is consistent with the proposed structure.

EXAMPLE 6: PREPARATION OF A SUBSTRATE CONTAINING A SULFATE BLOCK AT THE HYDROXYL GROUP OF 2-HYDROXYPHENYL-4-(3H)-QUINAZOLONE.

The following compound was prepared:

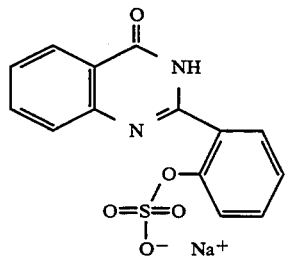

Synthesis of 2-(2-hydroxysulfonyloxy)-4-(3H)-quinazolinone, sodium salt. Chlorosulfonic acid (0.33 g, 2.5 mmoles) is added to 188 μL pyridine at 0° C. followed by 2-(2-hydroxyphenyl)-4-(3H)-quinazolinone (1a) (0.6 g, 2.5 mmoles). The mixture is heated at 60° C. for 24 hours. The pyridine is removed in-vacuo and the residue is redissolved in water. The solution is neutralized to pH 7.0 with NaOH and the product is purified by chromatography on a 3 cm×30 cm column of lipophilic Sephadex LH 20 using water for elution. The product-containing fractions are combined and lyophilized to a colorless solid. TLC: (10:5:1 ethyl acetate:methanol:water) R$_f$=0.3.

EXAMPLE 7: PREPARATION OF A SUBSTRATE CONTAINING A PHOSPHATE BLOCK AT THE HYDROXYL GROUP OF 2-HYDROXY-5'-CHLORO-PHENYL-4-(3H)-6-CHLORO-QUINAZOLONE.

The following compound was prepared by two different routes:

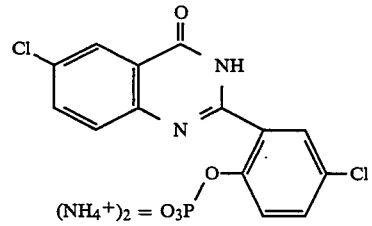

Synthesis of Ammonium 2-(5'-chloro-2'-phosphoryloxyphenyl)-6-chloro-4-(3H)-quinazolinone (8e). 2-(5'-Chloro-2'-hydroxyphenyl)-6-chloro-4-(3H)-quinazolinone, 1.53 g (5.0 mmoles) is added to 10 mL dry pyridine at 0° C. followed by 0.767 g (0.466 mL, 5 mmoles) phosphorus oxychloride, dissolved in 5.0 mL dry pyridine under N$_2$ (g) at 0° C. The reaction is complete within 2 minutes (silica gel TLC; ethyl acetate:methanol:water 7:1:1). The solution is neutralized to pH 7.0 by the addition of 0.68 ml (10 mmoles) concentrated ammonium hydroxide in 20 ml H$_2$O. The product is purified by chromatography on a 5 cm×17 cm column of (35–70μ) silica gel. Elution of the column is carried out with a stepwise gradient, starting with ethyl acetate (1000 mL) followed by ethyl acetate:methanol:water 7:1:1 (1750 mL). Fractions containing the product are combined. The solvent is removed by rotary evaporation and the product is dissolved in water and lyophilized (563 mg, 29% yield). TLC: R$_f$=0.17 (7:1:1 ethyl acetate:methanol:water). $^1$H NMR (DMSO-d$_6$)δ: 7.39 (d, 1H); 7.57 (d, 1H); 7.70–7.90 (m, 3H); 8.07 (s, 1H). $^{31}$P NMR (DMSO-d$_6$)δ: 1.2 (s).

Ammonium 2-(5'-chloro-2'-phosphoryloxyphenyl)-6-chloro-4-(3H)-quinazolinone. 2-(5'-Chloro-2'-hydroxyphenyl)-6-chloro-4-(3H)-quinazolinone, 122 mg (0.4 mmole) is added to (25 mL) methylene chloride at room temperature followed by 1H-tetrazole (84 mg) and di-t-butyl-N-N diethylphosphoramidite (160 mg). This mixture is allowed to stir for 1 hour, after which time the phosphite product is oxidized to the phosphate using m-chloroperbenzoic acid (160 mg). The product is isolated by vacuum filtration and is purified by chromatography (5×17 cm column, 35–70μ silica gel) using chloroform for elution. The product-containing fractions are combined and the solvent is removed in-vacuo. The residue is dissolved in acetonitrile (25 mL) containing trimethylsilylimidazole (10 Eq). The reaction is quenched by the addition of H$_2$O containing two equivalents of ammonium hydroxide. The product mixture is separated on a column 3×30 cm lipophilic Sephadex LH 20. TLC: (7:1:1 ethyl acetate:methanol:water) R$_f$=0.17.

Phosphates of other phenolic dyes are prepared by similar chemistry, of which the phosphorous oxychloride procedure is usually the preferred route.

EXAMPLE 8: PREPARATION OF A SUBSTRATE HAVING A GUANIDINOBENZOATE ESTER BLOCK AT THE 2-POSITION OF 2-HYDROXYPHENYL-4-(3H)-QUINAZOLONE.

The following compound was prepared:

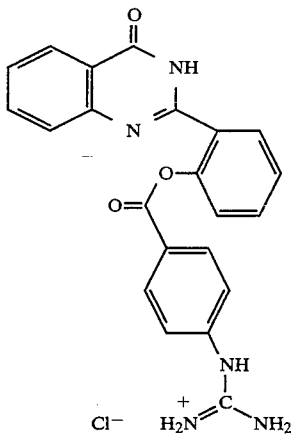

Synthesis of 2-(2-p-guanidinobenzoyloxy)-4-(3H)-quinazolone. Under anhydrous conditions a mixture of 2-(2-hydroxyphenyl)-(3H)-quinazolone (1a)(1.00 g, 4.2 mmole), dicyclohexylcarbodiimide (2.17 g, 10.52 mmole), and p-guanidinobenzoic acid (1.50 g, 9.69 mmole) in anhydrous dimethylformamide (25 mL) and dry pyridine (25 mL) are allowed to stir at room temperature for 18 hours. After this time the reaction mixture is filtered, evaporated to a clear yellow oil and crystallized by trituration with chloroform (70 mL). The resulting colorless nonfluorescent solid (2.24 g) is purified by reversed phase MPLC chromatography to yield the pure product which is characterized by $^1$H NMR.

EXAMPLE 9: PREPARATION OF A SUBSTRATE HAVING AN ESTER BLOCK AT THE HYDROXYL GROUP OF 2-HYDROXYPHENYL-4-(3H)-QUINAZOLONE.

The following compound was prepared:

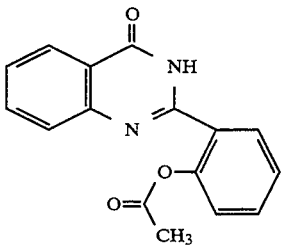

Synthesis of 2-(2-acetoxyphenyl)-4-(3H)-quinazolone. A suspension of 2-(2-hydroxyphenyl)-4-(3H)-quinazolone (1a)(25 mg, 0.1 mmole) in acetic anhydride (2 mL) is heated to reflux for 2 hours, cooled to room temperature, and the excess acetic anhydride is removed by vacuum distillation below 40° C.). The resulting solid is dissolved in chloroform and purified by silica gel chromatography using elution with chloroform to yield an off-white powder. TLC (SiO$_2$) (eluent=chloroform) R$_f$=0.14. 1H-NMR (CDCl$_3$)δ: 8.31(d,1H); 8.07(d,1H); 7.81(m,2H); 7.62-7.50(m,2H); 7.44(dd,1H); 7.27(dd, 1H); 2.32(s,3H,—OAc). The octanoate is prepared similarly.

EXAMPLE 10: PREPARATION OF A SUBSTRATE HAVING AN ETHYL ETHER BLOCK AT THE HYDROXYL GROUP OF 2-HYDROXYPHENYL-4-(3H)-QUINAZOLONE.

The following compound was prepared:

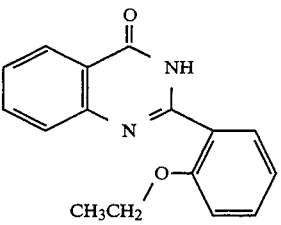

Synthesis of 2-(2-ethoxyphenyl)-4-(3H)-quinazolone. An equimolar mixture of anthranilamide (136 mg, 1.0 mmole) and 2-ethoxybenzaldehyde (166 mg, 1.0 mmole) is suspended in methanol (30 mL) and heated to reflux for 3 hours. After cooling, the Schiff's base is isolated by vacuum filtration, suspended in ethanol (50 mL) containing p-toluenesulfonic acid (33 mg, 0.17 mmole), and heated to reflux for 1 hour. The resulting dihydroquinazolone is treated with 2,3-dichloro-5,6-dicyano-1,4-benzoquinone (DDQ, 227 mg, 1.0 mmole) and heating is continued as above for 1 hour. After cooling to room temperature, the precipitated solid is filtered and washed with methanol. The product is recrystallized from methanol to yield a colorless solid. $^1$H-NMR (CDCl$_3$)δ:8.54 (d, 1H); 8.30 (d, 1H); 7.77 (m,2H); 7.51–7.43 (m,2H); 7.15 (t, 1H); 7.05 (d,1H); 4.30 (q,2H,—CH$_2$CH$_3$); 1.60(t,3H,—CH$_2$CH$_3$).

EXAMPLE 11: CHARACTERIZATION OF THE FLUOROGENIC SUBSTRATES AND THE FLUORESCENT PRODUCTS IN SOLUTION AND IN SUSPENSION.

1). Solubility. All of the subject substrates for phosphatase, sulfatase, glucuronidase and guanidinobenzoatase are highly soluble and nonfluorescent in water. Other glycosidase substrates show variable water solubility and are preferably prepared as stock solutions in an organic solvent such as dimethylsulfoxide (DMSO) which can then be added to the enzyme-containing sample in an appropriate buffer. Substrates for esterase and oxidase enzymes are nonfluorescent and tend to have low water solubility. They are preferably dissolved in DMSO before addition to the enzyme-containing sample.

2). Fluorescence spectral characterization of the solids. Since the fluorescent dyes that are formed on removal of BLOCK have very low aqueous solubility, it is difficult to directly disperse the solids in buffer for spectral determination. An alternative procedure is necessary for generating this information. When substrates containing the polar BLOCK group, phosphate, are hydrolyzed by the enzyme, the resulting products are much less soluble and are present in water as a fine dispersion of fluorescent precipitates. Since a turbid sample is normally unacceptable for optical measurement, fluorescence spectra of a fluorescent precipitate should be measured at a concentration as low as possible. Usually a concentration around the critical concentration required to commence precipitation (with an optical density less than 1.0) is used. The required concentration can easily be obtained by reacting the same concentration of substrate with an excess of alkaline phosphatase (Calzyme Laboratories, Inc., San Luis Obispo, Calif.) in a reaction buffer (0.1M TRIS pH 10.3 containing 50 mM NaCl, 10 mM MgCl$_2$ and 0.1 mM ZnCl$_2$). Fluorescence excitation and emission spectra of the reacted substrate sample are measured in a 1-cm cuvette and in a Perkin-Elmer LS-50 fluorometer using normal fluorescence spectrum acquisition procedures. Spectra for some of these compounds thus obtained are tabulated in Tables above.

3). Determination of the critical concentration and pH dependence for the precipitation. The critical concentration ($M_c$, in units of mmoles) and the pH dependence ($pK_a$) for precipitation are both important parameters for judging the precipitation properties of the enzymatic products obtained from the subject substrates. Below the critical concentration the product will not be detected as a fluorescent precipitate. Obviously these two parameters contribute to the precipitation in a correlated way. As a simple approach, one may define the critical concentration as the concentration necessary for the precipitation at a high pH where all of the phenol group is ionized. Similarly, acidification by lowering the pH results in precipitation at a concentration below the critical concentration that is obtained at high pH to an extent that is related to the $pK_a$ of the phenolic group. It is a characteristic of the preferred substrates that only the product precipitate is fluorescent. In this case the precipitate is quantitated by its fluorescence which results in a correlation of the fluorescence with the degree of precipitation.

To obtain the critical concentration for one product the phosphatase substrate (1e) (200 μL) in a 96-well plate is added to 0.1M TRIS, pH 10.3, containing 50 mM NaCl, 10 mM $MgCl_2$ and 0.1 mM $ZnCl_2$ to yield a final concentration of 0.1 to 10 mM. 50 μL of a 1 mg/mL solution of alkaline phosphatase is then added. The fluorescence development is complete after 5 minutes as measured in using a CytoFluor TM 2300 fluorescence plate reader (Millipore, Bedford, Mass.). A concentration showing appreciable fluorescence is determined as the critical concentration.

In a 96-well plate, 150 μL of the substrate solution at a final concentration below the critical concentration as determined above is combined with 50 μL 1 mg/mL alkaline phosphatase for sufficient time to allow complete substrate hydrolysis. The solutions are acidified with 50 μL HCl at concentrations appropriate for adjusting the pH of the reaction mixture from 10.3 to 2.0. The fluorescence is read in the CytoFluor apparatus. The pH showing half maximal fluorescence is the observed $pK_a$ of the substrates.

Alternatively the critical concentration and the $pK_a$ can be determined in a cuvette by measuring light scattering of the product precipitate using a spectrophotometer or a fluorometer.

4). Kinetic assay of some of the substrates. The specific activity ($k_2$, in a unit of micromole per minute per milligram protein) and Michaelis constant ($K_M$, in a unit of millimole) for hydrolysis of the substrates by the enzyme are listed in Table 10. All of the specific enzymatic reactions are made in the following buffers:

For β-galactosidase: 0.1M phosphate, pH 7.0 containing 0.11M 2-mercaptoethanol and 1 mM $MgCl_2$.

For alkaline phosphatase: 0.1M TRIS pH 10.3 containing 50 mM NaCl, 10 mM $MgCl_2$ and 0.1 mM $ZnCl_2$.

For acid phosphatase: 0.1M acetate pH 5.0.

For sulfatase: 0.1M acetate pH 5.0.

Because the kinetic assay involves variable amounts of precipitate with variable light scattering, measurement in the fluorometer as described above cannot be used here. Instead, a fluorescence plate reader with front-face measurement geometry such as the CytoFluor TM 2300 (Millipore, Bedford, Mass.) is preferred for quantitating the precipitate. The following protocol illustrates the kinetic assay.

4.1). In a 96-well plate, pipette 200 μL of a phosphatase substrate in the alkaline phosphatase reaction buffer with a final concentration of 2 to 6 mM, then add 50 μL 1 mg/mL alkaline phosphatase. The total hydrolysis of the substrate is usually complete within 5 minutes. Fluorescence of the precipitate is measured in the CytoFluor with appropriate sensitivity and excitation and emission settings as have been determined with the fluorometer. The fluorescence signal versus the amount of the precipitate is then established for each substrate.

4.2). In a 96-well plate, pipette 200 μL of a phosphatase substrate solution in the reaction buffer with final concentrations from 2 to 30 mM. Add 50 μL 10 μg/mL alkaline phosphatase to initiate the enzymatic reaction. Read the fluorescence of the resulting precipitate after 10 minutes reaction time and calculate the precipitate formation rate per minute by use of the determined fluorescence signal versus the amount of the precipitate.

4.3). Perform double-reciprocal plots of the substrate concentrations and the precipitate formation rate to obtain the specific activity and Michaelis constant (Stryer, L., Biochemistry, pp. 189, W. H. Freeman and Company, New York, 1988).

Measurement of the kinetic parameters of the substrates for other enzymes is done similarly.

Alternatively, in principle, turbidity or light scattering measurements in a spectrophotometer or a fluorometer can be used to quantitate the amount of precipitate in the cuvette. If a fluorometer is used, the excitation and emission should be set at a same wavelength.

EXAMPLE 12: IN VITRO ASSAYS OF BIOLOGICAL SAMPLES SUCH AS CELL EXTRACTS, SERA, TISSUE PREPARATIONS OR BIOPSY SAMPLES FOR ENZYMATIC ACTIVITY USING THE FLUORESCENT PRECIPITATING SUBSTRATES.

1). Solution assay of enzymatic activity. In this case the substrates react with the enzyme samples and the resulting fluorescence and/or turbidity of the hydrolytic products is measured in a fluorometer or a fluorescence plate reader for quantitating the enzymatic activity. For instance, acid or alkaline phosphatase activity can be quantitated in solution by use of a high concentration of one of the subject phosphatase substrates such the a quinazolone phosphates (1e–9e). For determination in the CytoFluor fluorescence plate reader, 200 μL of a quinazolone phosphate with concentrations from 5 to 10 mM in the reaction buffer best suited for the type of phosphatase activity to be measured is pipetted into a 96-well plate. Subsequently 50 μL of standard (purified) acid or alkaline phosphatase or the sample to be tested is added to the substrate solution. At 10 to 30 minutes reaction time, fluorescence of the hydrolysis precipitate is read in the CytoFluor apparatus. There is good linearity between the fluorescence resulting from the hydrolysis product generated by alkaline phosphatase activity when 1 ng to 5 μg of purified calf intestine alkaline phosphatase is used. Since the precipitate formation is favored by acid, similar results are obtained with various acid phosphatase enzymes using the identical substrates. This linearity is then used as a standard curve for determining the phosphatase activity in a sample from other biological sources. A similar determination can be performed using a cuvette by measuring the turbidity of the precipitated hydrolysis product in a spectrofluorometer.

2). Solid-phase detection of enzymatic activity ("dot blots" and related techniques). Solid-phase detection techniques are performed by immobilizing the enzymes being detected on a suitable membrane such as a nitrocellulose membrane. The immobilized enzymes react with a solution of the fluorescent precipitating substrate to yield distinct fluorescent spots on the membrane.

Enzymes from various biological sources are readily immobilized on an Immobilon-P membrane (Millipore, Bedford, Mass.) with retention of activity. After spotting the samples at a range of concentrations using a micropipet the spots are allowed to air dry for at least 10 minutes and the resulting membrane is incubated in the substrate solution. Detection is very sensitive. For example, the activity of 0.5 ng of purified calf intestine alkaline phosphatase can be easily visualized using a conventional UV-lamp (EX 365 nm) with even lower levels detectable over background using intensification equipment.

EXAMPLE 13: DETECTION OF ENZYMATIC ACTIVITY IN SAMPLES SEPARATED BY A CHROMATOGRAPHIC TECHNIQUE $\beta$-galactosidase from E. coli (MW 540,000, approximately 1 mg) and $\beta$-glucuronidase from E. coli (MW 280,000, approximately 1 mg) are dissolved in 25 $\mu$L of 0.1M phosphate, pH 7,0 containing 0.11M 2-mercaptoethanol and 1 mM MgCl$_2$ and chromatographed on a 1×35 cm column of BioGel A 1.5M equilibrated with the same buffer. Detection of the protein absorption at 280 nm is used to detect isolated protein fractions. This results in two well-separated peaks. To 25 $\mu$L aliquots of each fraction, is separately added 5 $\mu$L of a 5 mg/mL aqueous solution of 2-(5'-methoxy-2'-galactopyranosyl)-phenyl-4-(3H)-quinazolone (3h) or 2-(2-O-$\beta$-D-glucopyranosiduronic acid)-4-(3H)-quinazolone (4h). Visible yellow fluorescent precipitate formation occurs when the galactoside substrate is added to fractions that contain the first peak whereas visible formation of a green fluorescent precipitate occurs when the glucuronide is added to the fractions that contain the second peak. No cross reactivity is observed.

EXAMPLE 14: DETECTION OF ENZYMATIC ACTIVITY IN NON-DENATURING GELS FOLLOWING ELECTROPHORETIC SEPARATION.

1 ). Detecting enzymes on native gels using precipitating substrates. Gel electrophoresis is a common method for identifying proteins in fluids and tissue homogenates. In native gel electrophoresis, the proteins retain their activity during the process of separation and thus can hypothetically be identified by activity assays. By incubating the native gel with various precipitating substrates specific for the analyte enzyme, one can identify whether the enzyme is present in the loaded sample. These methods are used for investigating the expression of both endogenous enzymes and enzyme-fusion proteins and for the detection of the enzyme in samples suspected of containing the enzyme. A protocol commonly used in these experiments is as follows:

1. The enzyme-containing sample is mixed with the sample buffer (0.075M TRIS-HCl in 50% glycerol, pH 6.8) to a concentration that is appropriate for loading the enzyme. The sample is loaded onto a 4–20% gradient acrylamide gel. The gel is run at 30 mA for approximately 30 minutes.
2. The gel is incubated in a buffer that is optimal for the enzyme being detected and that contains 1 mM of the substrate. For alkaline phosphatase the buffer used is 100 mM MOPS, 50 mM NaCl, 1 mM MgCl$_2$, 0.1 mM ZnCl$_2$, pH 7.5. The appearance of fluorescent bands is monitored using a hand-held ultraviolet lamp.

2). Comparing the sensitivity of enzyme detection using precipitating substrates versus standard Coomassie Blue detection. Decreasing amounts of alkaline phosphatase are loaded into the lanes of two gels. The amount of alkaline phosphatase loaded into each lane varies from 5 $\mu$g to 10 $\mu$g. After electrophoresis, one gel is developed for visualization using standard Coomassie Blue-staining procedures; the other by incubation with 1 mM 8e as described above. The minimum detectable quantity of alkaline phosphatase using standard Coomassie Blue-staining methods is 1 $\mu$g. After incubation with 8e for 30 minutes, 1 ng of alkaline phosphatase is clearly visible using a handheld UV-lamp. After approximately 20 hours incubation, 0.25 ng of alkaline phosphatase can be visibly detected without any signal enhancement. These experiments indicate that incubation with the precipitating substrate provides a method for enzyme detection that is 4000 times more sensitive than standard Coomassie Blue-staining methods. As a negative control, it can be demonstrated that the alkaline phosphatase substrate does not stain lanes in an electrophoresed gel that are loaded with either 2-$\mu$g bovine serum albumin or 2-$\mu$g-$\beta$-galactosidase whereas the subject galactosidase substrates stain the galatosidase-containing lane but not the alkaline phosphatase band. Multiple proteins or extracts can be run in a single lane with only the enzyme specific for the synthetic substrate being detected by the staining.

EXAMPLE 15: LABELING OF AN ENZYME IN A LIVING CELL EXEMPLIFIED BY LABELING OF LACZ POSITIVE CELLS IN TWO DIFFERENT TYPES OF CELLS WITH A $\beta$-GALACTOSIDASE SUBSTRATE THAT YIELDS A FLUORESCENT PRECIPITATE.

1. Fibroblast Cells
    1.1 Cell Lines: NIH/3T3 cells (lacZ negative) and CRE BAG 2 cells (3T3 cells transformed with a retrovirus containing the lacZ gene) are employed for cellular assays. Both cell lines can be obtained from American Type Culture Collection Co., Rockville, Md. The cells are grown in a humidified atmosphere of 5% CO$_2$ in Dulbecco's modified Eagle's medium supplemented with 10% calf serum, 50 $\mu$g/mL gentamicin, 300 $\mu$g/mL L-glutamine and 10 mM HEPES pH 7.4.
    1.2 Stock Solution of the Labeling Reagent: The $\beta$-galactosidase substrate 1h is dissolved in DMSO to get a 10 mM stock solution.
    1.3 Working Medium: 100 $\mu$L of the dye stock solution is added to 10 mL of fresh culture medium to prepare a "working medium" containing 100 μM of the substrate 1h. This medium is then filter-sterilized by passing through an Acrodisc ™ filter (0.45μ pore size).

1.4 Staining and Examination of Cells: Cells grown on coverslips are transferred to the working medium and incubated at 37° C. under normal culture conditions. Cells are examined at the desired time for their fluorescence under a Zeiss microscope equipped with a Hoechst filter set (typically excitation at about 360 nm and emission past 480 nm). After 60 minutes of incubation, fluorescent spots can be observed in the cytoplasmic area in the lacZ positive CRE BAG 2 cells but not in the 3T3 cells. After 6 hours, the fluorescence intensity of stained CRE BAG 2 cells reaches its highest level.

1.5 Cytotoxicity and Cellular Retention: This substrate shows no cytotoxicity. Cells incubated in a 100 μM working medium of the galactosidase substrate 1h for 24 hours look morphologically normal and have the same population doubling time as the control. Cells preincubated in the working medium for 6 hours can be subcultured and incubated in fresh medium resulting in the formation of a second generation of cells that is normal and which does not contain the fluorescent precipitate.

2. Yeast Cells 2.1 Yeast Strain: Yeast strain EG 123 is transformed with plasmid pLGΔ-312S, which carries the yeast CYC1 promotor region and initiation codon fused in frame with the lacZ gene. The cells are grown in a synthetic medium selecting for plasmid maintenance to a density of about $10^7$ cells per mL. Cells are collected by centrifugation and resuspended in Z buffer to obtain a cell suspension. Z buffer contains 0.2% β-mercaptoethanol which improves the permeability of both the yeast cell wall and the plasma membrane. Nontransformed yeast cells are used as the control.

2.2 Staining Solution: The galactosidase substrate (1h) is first dissolved in DMSO to get 10 mM stock solution. This solution is diluted 1:50 with distilled water to obtain a 200 μM staining solution.

2.3 Staining and Examination of Cells: To inhibit endogenous vacuolar galactosidase activity, yeast cells are first preincubated with 300 μM chloroquine for 20 minutes at room temperature, then mixed with an equal volume of the substrate-containing staining solution. Most of the lacZ positive cells become fluorescent within 15 minutes. A crystalline precipitate can be observed in the cells, while the lacZ negative cells remain unstained for at least 2 hours.

EXAMPLE 16: WESTERN BLOT ANALYSIS USING A FLUOROGENIC SUBSTRATE FOR PHOSPHATASE THAT YIELDS A FLUORESCENT PRECIPITATE.

1). SDS-Gel Electrophoresis of Bovine Heart Cytochrome c Oxidase:

1.1. Cytochrome c oxidase from the bovine heart mitochondrial inner membrane is highly purified according to the method of Capaldi and Hayashi, FEBS LETT 26, 4229-4238 (1972).

1.2. 50 μl of pure cytochrome c oxidase (20 mg/ml) is dissolved in a dissociation buffer to a final concentration of 1 mg/ml for electrophoresis.

1.3. An 18% acrylamide gel containing 6M urea, 0.1% SDS is used for gel electrophoresis according to a procedure published by Zhang, Lindorfer and Capaldi, BIOCHEMISTRY, 27, 1389-1394 (1988). 15 μg of protein is loaded onto each lane. The subunits of cytochrome c oxidase are separated during electrophoresis (there are 13 different subunits in bovine cytochrome c oxidase).

1.4. The samples are prepared in three identical groups (A, B and C) so that the gel can be cut into three parts. Part A can be stained for Coomassie Blue visualization of the protein bands and parts B and C are used for the blot analysis.

2. Transfer of the Proteins from the Gel to a Nitrocellulose Membrane:

2.1. Immediately after electrophoresis, Part A of the gel is cut for Coomassie Blue staining.

2.2. Parts B and C of the gel are washed in a transfer buffer containing 20% methanol for 20 minutes at room temperature to remove the SDS from the gel. The nitrocellulose membrane is also thoroughly soaked in the transfer buffer prior to assembly of the "transfer sandwich".

2.3. Protein samples in both B and C, resolved in SDS-gel electrophoresis, are semi-dry transferred onto a nitrocellulose membrane following a standard electrophoretic elution procedure published by Harlow and Lane, ANTIBODIES, A LABORATORY MANUAL, Cold Spring Harbor Lab (1988).

2.4. The membrane is then washed with TRIS-buffered saline (TBS) and the additional protein binding sites on the membrane are saturated with 5% nonfat dry milk (blocking solution).

3. Immunodetection of specific polypeptides with a precipitating phosphatase substrate (1e) on nitrocellulose membranes:

3.1. The nitrocellulose membrane is incubated with a polyclonal antibody that is specific for Subunit II of Cytochrome C oxidase (final antibody concentration: 20 μg/ml) at room temperature for 12 hours with agitation.

The membrane is then washed with TRIS-buffered saline containing 0.1% Tween 20 (TTBS), to remove any unbound antibodies.

3.2. The membrane is incubated with the enzyme-labeled secondary antibody at room temperature for 1 hour with agitation. Alkaline phosphatase conjugated goat anti-rabbit antibodies are used with 1:3000 dilution in TTBS buffer containing 1% nonfat milk.

3.3. The membrane is washed with TTBS buffer to remove unbound secondary antibodies. This is then cut into two identical parts: B and C.

3.4. Membrane B is incubated in the phosphatase substrate BCIP/NBT (BioRad), while C is incubated with the fluorogenic, phosphatase substrate 1e.

4 Result:

4.1. After incubation for 15 minutes, the immunoreactive peptide band in membrane B is visualized by its blue color using BCIP/NBT staining. The staining on a membrane kept in a dry Petri dish fades within 3 days.

4.2. After 30 minutes, a bright fluorescent band of the immunoreactive subunit II is visualized under UV light in membrane C. The band, kept in a dry Petri dish, is still fluorescent after 3 days. No other transferred bands are stained on the membrane.

EXAMPLE 17: DETECTION OF A CELL SURFACE RECEPTOR FOR LECTINS.

1). Cells. NIH 3T3 cells (American Type Culture Collection, Rockville, Md.) are dish cultured then digested with trypsin and transferred onto glass coverslips. The cells are subcultured and stabilized on the slips for 12 to 24 hours before use.

2). Staining. The slips are transferred into a staining dish, washed with PBS, then rinsed in 3.7% formaldehyde PBS solution for 15 minutes at room temperature. The slips are washed with PBS, then incubated with 0.1 μg/mL biotinylated concanavalin A (Molecular Probes, Inc., Eugene, Oreg.) in PBS solution for 30 minutes at room temperature. The slips are washed with PBS buffer, then incubated with 1 μg/mL streptavidin alkaline phosphatase (Molecular Probes, Inc.) in a reaction buffer (0.1M TRIS pH 7.8 containing 0.15M NaCl, 50 mM $MgCl_2$ and 0.1 mM $ZnCl_2$) for 30 minutes at room temperature. The slips are washed with the reaction buffer, then incubated with 0.1 mM of a precipitating alkaline phosphatase substrate for 15 minutes at room temperature. The substrate is filtered through a 0.2 μM filter (Millipore, Bedford, Mass.) before use.

3). Detection. The slips are washed with PBS then examined under a Zeiss fluorescence microscope equipped with suitable filters (typically excitation at about 360 nm and emission past 480 nm). The product appears as brilliantly fluorescent spots that coincide with the cell with essentially no extracellular background. For comparison with a direct fluorescent conjugate, fixed cells are incubated with 0.1 μg/mL fluorescein isothiocyanate-conjugated concanavalin A (FITC-Con A) in PBS solution and subsequently washed with PBS. The FITC-Con A stained cells are much less bright than the cells stained with the precipitating substrates. Alternatively the fluorescent labeled cells can be detected and the fluorescence quantitated by flow cytometry.

EXAMPLE 18: DETECTION OF A GROWTH FACTOR RECEPTOR.

1). Cells. Dish-cultured A431 cells (American Type Culture Collection, Rockville, Md.) are digested with trypsin and transferred to glass cover-slips. The cells are subcultured and stabilized for 24 to 48 hours before use.

2). Staining. The slips are transferred into a staining dish, washed with PBS, rinsed in a 0.5% formaldehyde PBS solution for 15 minutes at room temperature, washed with PBS, then incubated in 50 ng/mL biotinylated epidermal growth factor (biotin-EGF; Molecular Probes, Inc., Eugene, Oreg.) in PBS solution for 30 minutes at room temperature. The slips are washed with PBS buffer, then incubated with 1 μg/mL streptavidin alkaline phosphatase (Molecular Probes, Inc.) in a reaction buffer (0.1M TRIS pH 7.8 containing 0.15M NaCl, 50 mM $MgCl_2$ and 0.1 mM $ZnCl_2$) for 30 minutes at room temperature. The slips are washed with the reaction buffer, then incubated with 0.1 mM of a precipitating alkaline phosphatase substrate in the reaction buffer for 15 minutes at room temperature. The substrate solution is filtered through a 0.2 μM filter (Millipore, Bedford, Mass.) before use.

3). Detection. The slips are washed with PBS then examined under a Zeiss fluorescence microscope equipped with suitable filters (typically excitation at about 360 nm and emission past 480 nm). The product appears as brilliantly fluorescent spots that are observed only in areas of the slide where the cell is observed with essentially no extracellular background. For comparison with a direct fluorescent conjugate, the fixed cells are incubated with 50 ng/mL solution of fluorescein EGF and subsequently washed with PBS. The fluorescein EGF stained cells have extremely low visibility and very low photostability which precludes their visualization. Alternatively the fluorescent labeled cells can be detected and the intensity quantitated by flow cytometry.

EXAMPLE 19: ENZYME-MEDIATED IMMUNOHISTOCHEMICAL DETECTION USING THE PRECIPITATING SUBSTRATES.

1). Cells and Detection Kit. A commercial diagnostic kit which is normally used to diagnose systemic lupus erythematosus (SLE) and related autoimmune diseases is adapted to demonstrate the utility of the precipitating substrates for enzyme-mediated histochemical detection. The kit includes slides containing wells of fixed HEp-2 cells (human epithelial cells) and a positive control consisting of anti-DNA antibodies isolated from humans with the disease. Normally, the slides are incubated with sera from patients and then probed with fluorescein-conjugated anti-human antibodies. Using this method, the nuclei of those cells that have been incubated with SLE-positive sera appear to have typical morphology that is identified by their green fluorescence using standard fluorescence microscopy whereas the negative controls have no fluorescence.

2). Sample Preparation. A four-step incubation protocol is used to prepare the slides. All reagents are diluted in 1% bovine serum albumin (BSA) in TRIS-buffered saline, pH 7.5 (TBS; 100 mM NaCl, 100 mM TRIS). Each incubation is ½ hour. Slides are washed three times with TBS between incubations. A typical procedure consists of the following steps:

1. The wells are incubated with either SLE-positive or -negative human sera (provided in the kit).
2. The wells are incubated with biotinylated goat anti-human (20 μ/ml).
3. The wells are incubated with streptavidin (50 μg/mL), a reagent that has four binding sites for biotin. Excess binding sites are available for binding the next reagent.
4. The wells are incubated with a biotinylated enzyme that will remove BLOCK from the subject substrates. Typical enzymes are biotinylated alkaline phosphatase or biotinylated β-galactosidase both used at about 20 μg/ml.

Alternatively, numerous other combinations are possible including the single reagent of an enzyme-coupled anti-human antibody, in which steps 2, 3 and 4 are combined.

3). Staining with the precipitating substrate. In the preceding steps, a series of molecules is effectively bound to the nuclei of those cells that are initially incubated with SLE-positive sera. The final molecule in the series is an enzyme that will cleave its substrate to form a fluorescent precipitate that is deposited directly over the nuclei of the HEp-2 cells. The protocol in part 2 of this example is followed by a 30 minute incubation in a suitable substrate typically at 0.1 to 3 mM but preferably about 1 mM in a solution that is optimized for the given enzyme and for the substrate. For alkaline phosphatase and the substrate 8e this is about 100 mM MOPS, 50 mM NaCl, 10 mM $MgCl_2$ and 0.1 mM $ZnCl_2$, pH 7.5. Those cells that are initially incubated with SLE-positive sera have brightly fluorescent nuclei using a standard fluorescence microscope equipped with filters appropriate to the dye, No signal is detected in those wells initially incubated with the negative sera.

EXAMPLE 20: DETECTION OF IN SITU HYBRIDIZATION.

I. Target and probes. The following procedures illustrate the detection of human actin m-RNA and genomic genes. The cells used are human epidermoid carcinoma (A431, American Type Culture Collection) and NIH 3T3 cells. The actin probe is 5'-biotin dX CAC GGA GTA CTT GCG CTC AGG AGG AGC prepared on an Applied Biosystems DNA Synthesizer.

II. Reagents. The following reagents are required:
Buffer Concentrates:
  A) 1 L of 20×SSC buffer concentrate (3M NaCl and 0.3M $Na_3$ citrate, pH 7.0): 175.2 g NaCl, 88.2 g $Na_3$ citrate and 1 liter water, brought to pH 7.0 using HCl.
  B) 1 L of 1M TRIS (1M TRIS and 1.5M NaCl, pH 7.8): 121 g TRIS base, 87.6 g NaCl, brought to pH 7.8 with HCl.

Working Buffers:
  1) 100 mL Buffer 1 (fixation buffer, 3.7% formaldehyde in PBS): 10 mL 37% formaldehyde mixed with 90 mL PBS.
  2) 100 mL Buffer 2 (permeabilization buffer, 0.1% Triton X-100 in PBS): 0.1 mL concentrated Triton X-100 dissolved in 100 mL PBS.
  3) 100 mL Buffer 3 (RNA digestion buffer, 2×SSC): 10 mL 20×SSC mixed with 90 mL water.
  4) 100 mL Buffer 4 (hybridization buffer, 25 mM $NaH_2PO_4.H_2O$, pH 6.5, 50% formamide, 2×SSC, 2×Denhardt, 0.1 mg/mL calf thymus DNA, 0.1 mg/mL E. coli t-RNA and 15% dextran sulfate).

Following is a preparation procedure for Buffer 4:
Dissolve 10 mg calf thymus DNA (Sigma #1501) in 2 mL water by sonication until a clear homogenous solution is obtained (this requires about 20 minutes in a water sonication bath). Dissolve 345 mg $NaH_2PO_4.H_2O$ in about 35 mL water and bring the pH to 6.5 with NaOH. In a measurement cylinder, add the phosphate buffer (about 35 mL), the sonicated DNA, 10 mg t-RNA (Sigma #1753), 10 mL 20×SSC, 2 mL 100×Denhardt, 50 mL formamide (Sigma #7503) and water compensated to 100 mL volume. This step yields a pre-hybridization solution. Dissolve 15 g dextran sulfate (Sigma #8906) in the pre-hybridization solution. This is the final hybridization buffer.

5) 100 mL Buffer 5 (post-hybridization buffer, 7×SSC and 65% formamide): 35 mL 20×SSC and 65 mL formamide (Sigma 7503).
  6) 1 L Buffer 6 (detection buffer, 1/10 TBS, 1% BSA and 0.1% Tween 20): 100 mL TBS, 10 g BSA and 1 mL Tween 20 dissolved in 900 mL water.
  7) 100 mL Buffer 7 (non-BSA wash buffer, 1/10 TBS and 0.1% Tween 20): 10 mL TBS and 0.1 mL Tween 20 dissolved in 90 mL water.
  8) 100 mL Buffer 8 (reaction buffer, 1/10 TBS, 50 mM $MgCl_2$ and 0.1 mM $ZnCl_2$): 10 mL TBS, $MgCl_2.6H_2O$ and 0.1 mL 15 mg/mL $ZnCl_2$ solution dissolved in 90 mL water.
  9) 1 L phosphate buffered saline (PBS).

III. Staining Procedures.
  1) Two slips of 3T3 cells and 4 slips of A431 cells are placed in the staining dishes with a cover glass then the cells are washed with PBS.
  2) The cells are fixed by adding Buffer 1 at room temperature for 15 minutes then are washed with PBS.
  3) The cells are permeabilized by adding Buffer 2 at room temperature for 15 minutes, washed with PBS and then washed with buffer 3.
  4) Two of the A431 slips are incubated with 0.1 mg/mL RNase A Buffer 3 solution (prepared from 10 mg Sigma #5500 RNase A in 10 mL Buffer 3); the rest of the slips are incubated with Buffer 3. The incubation is done at 37° C. for 60 minutes. All of the slips are then washed with Buffer 3.
  5) The biotin-labeled actin probe solution is prepared at 0.25 µg/mL in 24 mL Buffer 4 (60 µL of 100 µg/mL actin probe stock solution is dissolved in 24 mL buffer 4). The cell slips are rinsed in 8 mL of the probe solution at 37° C. for 10 minutes for preincubation. The cell slips are placed in a 100° C. oven for 20 minutes, then placed back on the 37° C. incubator to proceed with the hybridization for 10 to 20 hours.
  6) The hybridization is stopped by removing the probe solution and then the cell slips are post-washed 4 times with Buffer 5 at 37° C. for 10 minutes.
  7) A streptavidin alkaline phosphatase conjugate is prepared at 0.6 µg/mL in 24 mL Buffer 6 (24 µL 0.6 mg/mL stock solution dissolved in 24 mL Buffer 6). The cell slips are rinsed in the conjugate solution at 37° C. for 30 minutes.
  8) The cell slips are thoroughly washed 3 times with Buffer 6, 3 times with Buffer 7 and 3 times with Buffer 8.
  9) A 1.5 mM solution of the fluorescent precipitating substrate for alkaline phosphatase is prepared in 24 mL Buffer 8 (1.2 mL of the substrate 30 mM in DMSO stock solution is dissolved in 24 mL Buffer 8 that is further filtered with 0.2 µm filter made by Millipore). The cell slips are rinsed in the substrate solution, and left at room temperature for 45 minutes to complete the enzymatic reaction.
  10) The reaction is stopped and the cell slips are washed with PBS.
  11) The cell slips are mounted for examination by fluorescence microscopy.

Modifications familiar to one skilled in the art permit use of detection reagents such as alkaline phosphatase-conjugated antibodies to digoxigenin to detect digoxigenin labeled probes, β-galactoside-conjugated avidins to detect biotinylated probes or alkaline phosphatase substrates to detect direct alkaline phosphatase-labeled probes.

EXAMPLE 21: USE OF THE FLUORESCENT PRECIPITATING SUBSTRATES IN CELL ANALYSIS AND SORTING BY FLOW CYTOMETRY.

Basically, cytometry experiments consist of two major steps: 1) cell preparation and labeling; 2) cell analysis (and sorting if desired) in a flow cytometer. The first step includes preparing a homogeneous cell suspension and appropriate cell staining with the precipitating substrates. The staining conditions typified by Con A and EGF receptors in Examples 17 and 18 may be referenced. However one must use a centrifuge to wash the cell suspension being evaluated. In addition, if an intracellular component is analyzed in a living cell such as the lacZ expression in Example 16, the substrate concentration for final staining should be raised to 1 to 1.5 mM to compensate for the substrate's slower diffusion into cells.

The second step includes selection of a cytometer, sorter and laser source that should be able to excite the dye near its absorption maximum, compensate for cell autofluorescence and determine cell velocity and other instrumental conditions depending on the specific research purpose. Several of the subject dyes are excited in the ultraviolet near 360 nm and the high Stokes shift makes the autofluorescence relatively low. The discrimination against background is further improved by the enhanced signal from the enzymatic amplification. These properties permit detection of rare binding events and detection in the presence of a significant fluorescence background.

Precipitation of the fluorescent product from solution permits detection of the fluorescent product adsorbed to the surface of the cell, even if the cell is living or in a flowing solution. Any precipitated particles that are not associated with the cell can be separately determined and disregarded by their different light scattering properties. These reagents and techniques permit amplification of the signal over that obtained using direct fluorescent conjugates.

It is to be understood that, while the foregoing invention has been described in detail by way of illustration and example, numerous modifications, substitutions, and alterations are possible without departing from the spirit and scope of the invention as described in the following claims.

What is claimed is:

1. A method for detecting the activity of an enzyme comprising:
   a) combining a sample suspected of containing the enzyme, with a substrate of the formula:

(BLOCK-O-)—$X_{fl}$ where BLOCK is a blocking group that is capable of being cleaved from the remainder of the substrate by action of the enzyme resulting in a visible precipitate of the formula:

H—O—$X_{fl}$ where $X_{fl}$ has the structure:

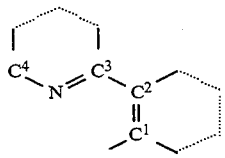

where carbon atoms of —$C^1$=$C^2$— are further joined so as to complete a first 5- or 6-membered aromatic ring which may contain at least one of the hetero atoms N, O or S, where carbon atoms of —$C^4$—N=$C^3$— are further joined so as to complete a second 5- or 6-membered aromatic ring that contains at least the nitrogen between $C^3$ and $C^4$ and may contain at least one additional hetero atom N, O or S, where the first and second aromatic rings may be joined by a 5- or 6-membered bridging ring that contains at least the $C^2$ from the first aromatic ring and the $C^3$ from the second aromatic ring, which bridging ring may be saturated or unsaturated and may contain a hetero atom N, O, or S, where each of the first and second aromatic rings may be fused to at least one additional aromatic ring that may contain at least one of the hetero atoms N, O or S, and where each of said aromatic rings may be further modified by substitution of any hydrogens on an aromatic carbon by substituents that are halogen, nitro, cyano, aryl, lower alkyl (1–4 carbons), perfluoroalkyl (1–4 carbons), or alkoxy (1–4 carbons), or any combination thereof; and $X_{fl}$ is covalently linked to the oxygen —O— at $C_1$; under conditions suitable for formation of said visible precipitate; and b) qualitatively or quantitatively detecting the precipitate.

2. A method, as claimed in claim 1, where BLOCK is a monovalent moiety derived by removal of a hydroxy group from phosphate or sulfate, or a biologically compatible salt thereof; or a monovalent moiety derived by removal of a hydroxy group from an alcohol or from a carboxy group of an aliphatic, aromatic or amino acid or of a peptide; or a monovalent moiety derived by removal of an anomeric hydroxy group from a mono- or polysaccharide.

3. A method, as claimed in claim 2, wherein BLOCK is derived by removal of a hydroxy group from a carboxy group of an aliphatic, aromatic or amino acid or of a peptide.

4. A method, as claimed in claim 2, where BLOCK is derived from an alcohol or from a mono- or polysaccharide.

5. A method, as claimed in claim 2, where BLOCK is derived from phosphate or sulfate, or a biologically compatible salt thereof.

6. A method, as claimed in claim 1, where BLOCK is cleaved from the remainder of the substrate by a hydrolytic enzyme.

7. A method, as claimed in claim 6, where BLOCK is cleaved from the remainder of the substrate by a hydrolytic glycosidase or phosphatase enzyme.

8. A method, as claimed in claim 1, where BLOCK is cleaved from the substrate, resulting in formation of a fluorescent precipitate with excitation and emission characteristics different from those of said substrate.

9. A method, as claimed in claim 1, where H—O—$X_{fl}$ is a precipitate that has the structure:

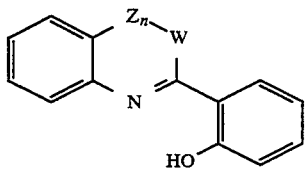

where Z is —(C=O)— or —CH=(methine) and n=1 or 0;
where W is (CH$_3$)$_2$C, —CH$_2$—, —CH=, S, O, or —(N—R)—, wherein R is H or lower alkyl containing 1-4 carbons; and
where each aromatic ring is optionally modified by substitution of one or more hydrogens on an aromatic carbon by halogen, lower alkyl (1-4 carbons), or alkoxy (1-4 carbons) substituents, or any combination thereof.

10. A method, as claimed in claim 9, wherein n=0.

11. A method, as claimed in claim 9, wherein $Z_n$ is —(C=O)— and W is —(N—R)—, wherein R is H or lower alkyl containing 1-4 carbons.

12. A method, as claimed in claim 1, where BLOCK is derived from phosphate and is capable of being cleaved from the remainder of the substrate by a phosphatase enzyme, resulting in a fluorescent precipitate of the formula:

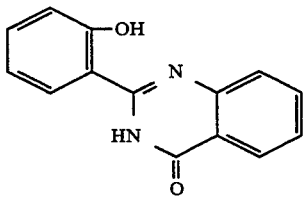

where each aromatic ring is optionally modified by substitution of one or more hydrogens on an aromatic carbon by substituents that are halogen, nitro, lower alkyl (1-4 carbons), or alkoxy (1-4 carbons), or any combination thereof.

13. A method, as claimed in claim 1, where BLOCK is derived from phosphate and is capable of being cleaved from the remainder of the substrate by a phosphatase enzyme, resulting in a fluorescent precipitate of the formula:

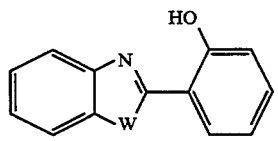

where W is S, O, or —(N—R)—, wherein R is H or lower alkyl containing 1-4 carbons; and
where each aromatic ring is optionally modified by substitution of one or more hydrogens on an aromatic carbon by substituents that are halogen, nitro, lower alkyl (1-4 carbons), or alkoxy (1-4 carbons), or any combination thereof.

14. A method, as claimed in claim 1, where BLOCK is derived from a mono- or polysaccharide, and is capable of being cleaved from the remainder of the substrate by a glycosidase enzyme, resulting in a fluorescent precipitate of the formula:

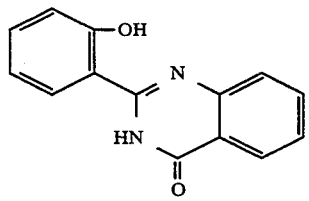

where each aromatic ring is optionally modified by substitution of one or more hydrogens on an aromatic carbon by substituents that are halogen, nitro, lower alkyl (1-4 carbons), or alkoxy (1-4 carbons), or any combination thereof.

15. A method, as claimed in claim 1, where BLOCK is derived from a mono- or polysaccharide, and is capable of being cleaved from the remainder of the substrate by a glycosidase enzyme, resulting in a fluorescent precipitate of the formula:

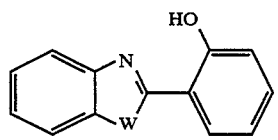

where W is S, O, or —(N—R)—, wherein R is H or lower alkyl containing 1-4 carbons; and
where each aromatic ring is optionally modified by substitution of one or more hydrogens on an aromatic carbon by substituents that are halogen, nitro, lower alkyl (1-4 carbons), or alkoxy (1-4 carbons), or any combination thereof.

16. A method, as claimed in claim 1, where the sample is combined with the substrate under conditions comprising:
incubating the sample in aqueous buffer at a pH greater than about 2 and less than about 11, with the substrate for a period of time sufficient to allow formation of the precipitate.

17. A method, as claimed in claim 16, where the precipitate is fluorescent and analyzing the precipitate comprises:
i) exposing the fluorescent precipitate to a light source capable of producing light at a wavelength of absorption of the fluorescent precipitate; and
ii) detecting the resultant fluorescence of the precipitate.

18. A method, as claimed in claim 1, where analyzing the precipitate comprises detecting the precipitate by visual inspection or light scattering techniques.

19. A method, as claimed in claim 1, where the sample comprises biological fluids, cell extracts, protein fractions, or purified enzymes.

20. A method, as claimed in claim 19, where the sample has been separated into its components by electrophoresis.

21. A method, as claimed in claim 1, for detecting activity of an intracellular endogenous enzyme where the sample is cells or tissues.

22. A method, as claimed in claim 21, where the sample is live cells or tissues.

23. A method, as claimed in claim 21, further comprising identifying and sorting cells or tissues that contain the precipitate.

24. A method, as claimed in claim 23, where cells are identified and sorted using a flow cytometer.

25. A method, as claimed in claim 1, where the sample is combined with the substrate on an inert, solid or semi-solid matrix.

26. A method, as claimed in claim 25, where the matrix is a filter membrane, electrophoretic gel, or chromatographic medium.

27. A method, as claimed in claim 1, for detecting the activity of the enzyme as a conjugate where the enzyme is coupled to one member of a specific binding pair or of a series of specific binding pairs to form a complementary conjugate, which attaches to its complementary analyte to form a complementary binding complex.

28. A method, as claimed in claim 27, where the complementary analyte is a protein, a nucleic acid, a carbohydrate or an antigen.

29. A method, as claimed in claim 27, where the complementary analyte is RNA or DNA.

30. A method, as claimed in claim 27, where one member of a specific binding pair or of a series of specific binding pairs is a nucleic acid of less than about 100 bases in length.

31. A method, as claimed in claim 27, where the enzyme is coupled to a nucleic acid.

32. A method, as claimed in claim 27, where the enzyme is coupled to an antigen or antibody.

33. A method, as claimed in claim 27, where the enzyme is coupled to biotin, anti-biotin, avidin or streptavidin.

34. A method, as claimed in claim 27, where the sample is cells or tissues.

35. A method, as claimed in claim 34, where the sample is live cells or tissues.

36. A method, as claimed in claim 34, further comprising identifying and sorting cells or tissues that contain the precipitate.

37. A method, as claimed in claim 36, where cells are identified and sorted using a flow cytometer.

38. A method for detecting the activity of an enzyme, comprising:
   a) combining a sample of cells suspected of containing the enzyme, with a substrate of the formula:

(BLOCK-O)—$X_{fl}$ where BLOCK is a blocking group that is a monovalent moiety derived by removal of a hydroxy group from phosphate, from sulfate or a biologically compatible salt thereof; or a monovalent moiety derived by removal of a hydroxy group from an alcohol or from a carboxy group of an aliphatic, aromatic or amino acid or of a peptide; or a monovalent moiety derived by removal of an anomeric hydroxy group from a mono- or polysaccharide; and is capable of being cleaved from the remainder of the substrate by action of the specific enzyme resulting in a fluorescent precipitate of the formula:

X—O—$X_{fl}$ where $X_{fl}$ has the structure:

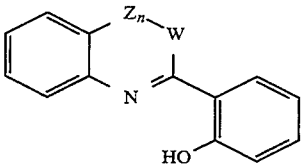

where Z is —(C=O)— or —CH=(methine) and n=1 or 0;
where W is $(CH_3)_2C$, —$CH_2$—, —CH=, S, O, or —(-N—R)—, wherein R is H or lower alkyl containing 1-4 carbons; and
where each aromatic ring is optionally modified by substitution of one or more hydrogens on an aromatic carbon by substituents that are halogen, nitro, lower alkyl (1-4 carbons), or alkoxy (1-4 carbons), or any combination thereof;
in aqueous buffer at a concentration of substrate between about 0.1 mM and about 5 mM at a pH less than about 8.5 for greater than 5 minutes;
   b) exposing the precipitate to a light source with a wavelength greater than about 300 nm; and
   c) detecting fluorescence of the precipitate at greater than about 400 nm.

39. A method for detecting the activity of an enzyme conjugate, comprising:
   a) combining a sample containing the enzyme that is incorporated in a specific binding complex, with a substrate of the formula:

(BLOCK-O)—$X_{fl}$ where BLOCK is a blocking group that is a monovalent moiety derived by removal of a hydroxy group from phosphate, from sulfate or a biologically compatible salt thereof; or a monovalent moiety derived by removal of a hydroxy group from an alcohol or from a carboxy group of an aliphatic, aromatic or amino acid or of a peptide; or a monovalent moiety derived by removal of an anomeric hydroxy group from a mono- or polysaccharide; and is capable of being cleaved from the remainder of the substrate by action of the specific enzyme resulting in a fluorescent precipitate of the formula:

H—O—$X_{fl}$ where $X_{fl}$ has the structure:

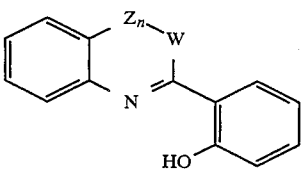

where Z is —(C=O)— or —CH=(methine) and n=1 or 0;
where W is $(CH_3)_2C$, —$CH_2$—, —CH=, S, O, or —(-N—R)—, wherein R is H or lower alkyl containing 1-4 carbons; and
where each aromatic ring is optionally modified by substitution of one or more hydrogens on an aromatic carbon by substituents that are halogen, nitro, lower alkyl (1-4 carbons), or alkoxy (1-4 carbons), or any combination thereof;
in aqueous buffer at a concentration of substrate between about 0.1 mM and about 5 mM at a pH less than about 8.5;
   b) exposing the precipitate to a light source with a wavelength greater than about 300 nm; and
   c) detecting fluorescence of the precipitate at greater than about 400 nm.

* * * * *

UNITED STATES PATENT AND TRADEMARK OFFICE
CERTIFICATE OF CORRECTION

PATENT NO. : 5,443,986
DATED : Aug. 22, 1995
INVENTOR(S) : Haugland et al.

It is certified that error appears in the above-indentified patent and that said Letters Patent is hereby corrected as shown below:

On the cover page, inventor "Haughland et al." should be --Haugland et al.--. Item [19].

On the cover page, inventor "Richard P. Haughland" should be --Richard P. Haugland--. Item [75].

In the abstract, the figure should appear as follows:

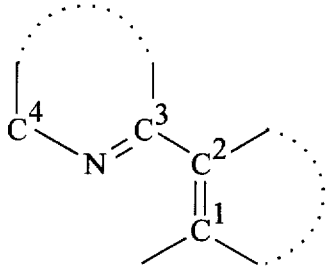

At Col. 7, lines 7-15, the figure should appear as follows:

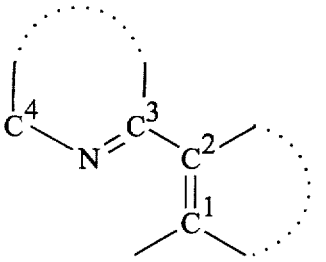

At Col. 13, line 48, "$X_n$" should be --$X_{fl}$--.

UNITED STATES PATENT AND TRADEMARK OFFICE
CERTIFICATE OF CORRECTION

PATENT NO. : 5,443,986
DATED : Aug. 22, 1995
INVENTOR(S) : Haugland et al.

It is certified that error appears in the above-indentified patent and that said Letters Patent is hereby corrected as shown below:

At Col. 15, Table 7, "Benzo 4-(3H)-quinazolinone-2l-phosphates" should be --Benzo 4-(3H)-quinazolinone-2'-phosphates--.

Signed and Sealed this

Seventeenth Day of March, 1998

Attest:

BRUCE LEHMAN

Attesting Officer

Commissioner of Patents and Trademarks